United States Patent [19]

Grimmell et al.

[11] 4,143,770
[45] Mar. 13, 1979

[54] METHOD AND APPARATUS FOR COLOR RECOGNITION AND DEFECT DETECTION OF OBJECTS SUCH AS CAPSULES

[75] Inventors: William C. Grimmell, Lake Hiawatha, N.J.; Jim M. Adams, Holtzminden, Fed. Rep. of Germany; Gilbert C. Kaetzel, Wayne, N.J.; Robert P. Fazzini, Nutley, N.J.; Edward F. DeZabala, Pequannock, N.J.

[73] Assignee: Hoffmann-La Roche Inc., Nutley, N.J.

[21] Appl. No.: 698,986

[22] Filed: Jun. 23, 1976

[51] Int. Cl.² ............................................ B07C 5/344
[52] U.S. Cl. ................................... 209/558; 209/564; 209/577; 209/580; 209/587; 209/644; 250/226; 356/237
[58] Field of Search ............ 209/73, 74 M, 75, 111.5, 209/111.6, 111.7 R; 250/223 R, 226; 198/397, 403, 404; 356/73, 156, 173, 178, 168, 237

[56] References Cited

U.S. PATENT DOCUMENTS

| | | | |
|---|---|---|---|
| 3,123,217 | 3/1964 | McMillan et al. | 209/111.5 |
| 3,373,870 | 3/1968 | Black et al. | 209/111.6 |
| 3,737,239 | 6/1973 | Adams et al. | 209/111.6 X |
| 3,757,943 | 9/1973 | Chae et al. | 209/111.7 R |
| 3,773,172 | 11/1973 | McClure et al. | 209/111.6 X |
| 3,991,605 | 11/1976 | Reuland | 209/72 X |

FOREIGN PATENT DOCUMENTS 1101957  2/1968  United Kingdom.

Primary Examiner—Joseph J. Rolla
Attorney, Agent, or Firm—Jon S. Saxe; Bernard S. Leon; Mark L. Hopkins

[57] ABSTRACT

Method and apparatus for high-speed automatic inspection and processing of large numbers of solid discrete particular objects such as multicolored capsule dose forms in regard to color and/or defect detection, in which virtually all unacceptable material is isolated and an accurate running and total count of acceptable material is provided. The objects are transported in a number of channels past respective optical heads comprising an electro-optics system, the transport mechanism being arranged to provide signals representative of relative object location. The electro-optics system is comprised operatively of separate color recognition and shape inspection subsystems. For the former, a plurality of optical channels are arranged in each optical head operatively in P groups of R optical channels each. The R optical channels of each group view different object segments to provide a spatially integrated output for minimizing noise and particularly the effects of printing on the objects. The P outputs constitute a multidimensional (vector) color signature. For defect detection, a pair of optical channels are provided with each optical head to provide signals constituting the shape signature of the object. The color and shape signature information of an object is obtained by sampling photodetector outputs in dependence on the object position information from the transport mechanism and also the sensed specular peak by a computer-controlled arrangement. The signatures obtained are compared to stored reference signatures for color and shape, and output signals are developed from the comparison which are transmitted to a reject arrangement for isolating the unacceptable material.

87 Claims, 33 Drawing Figures

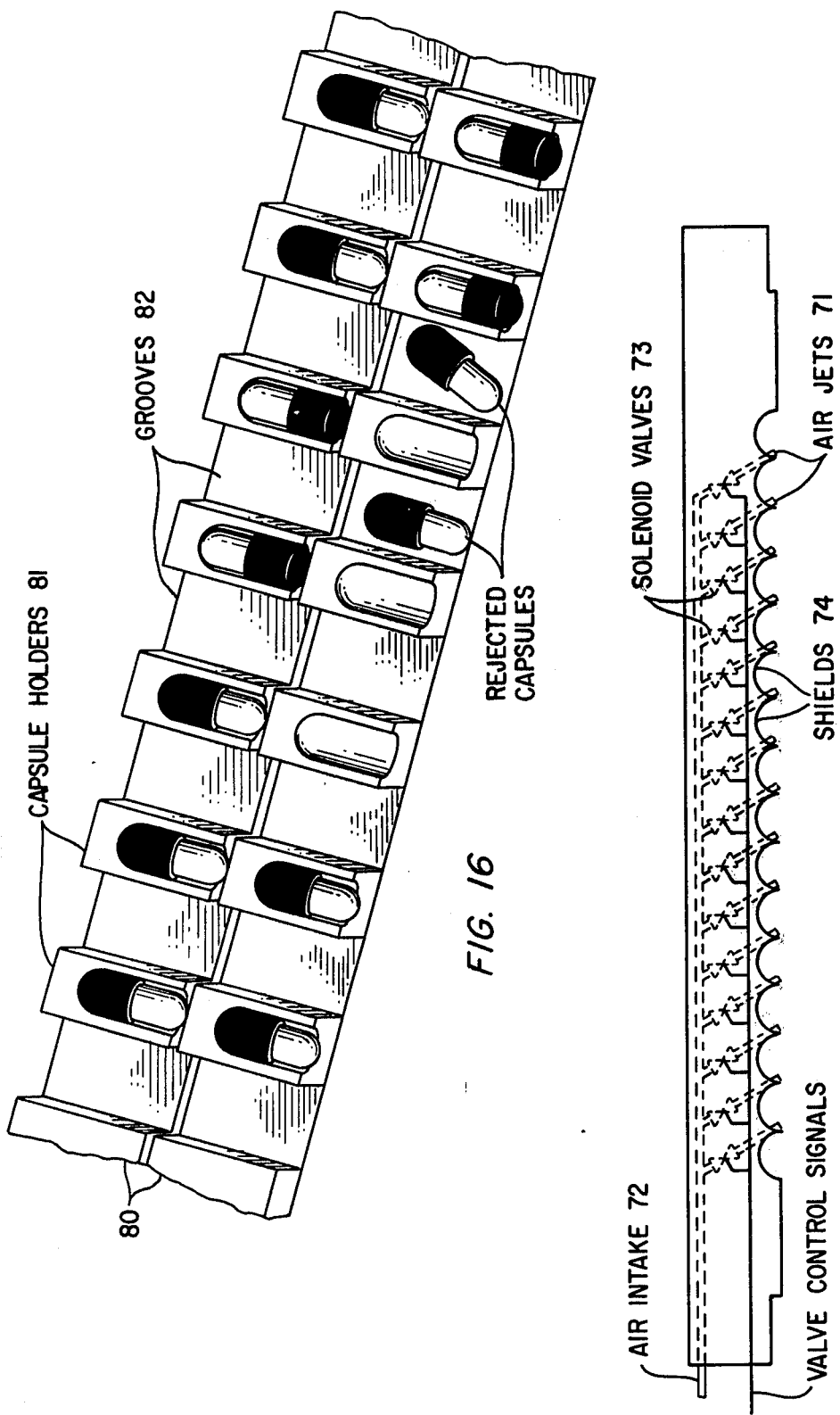

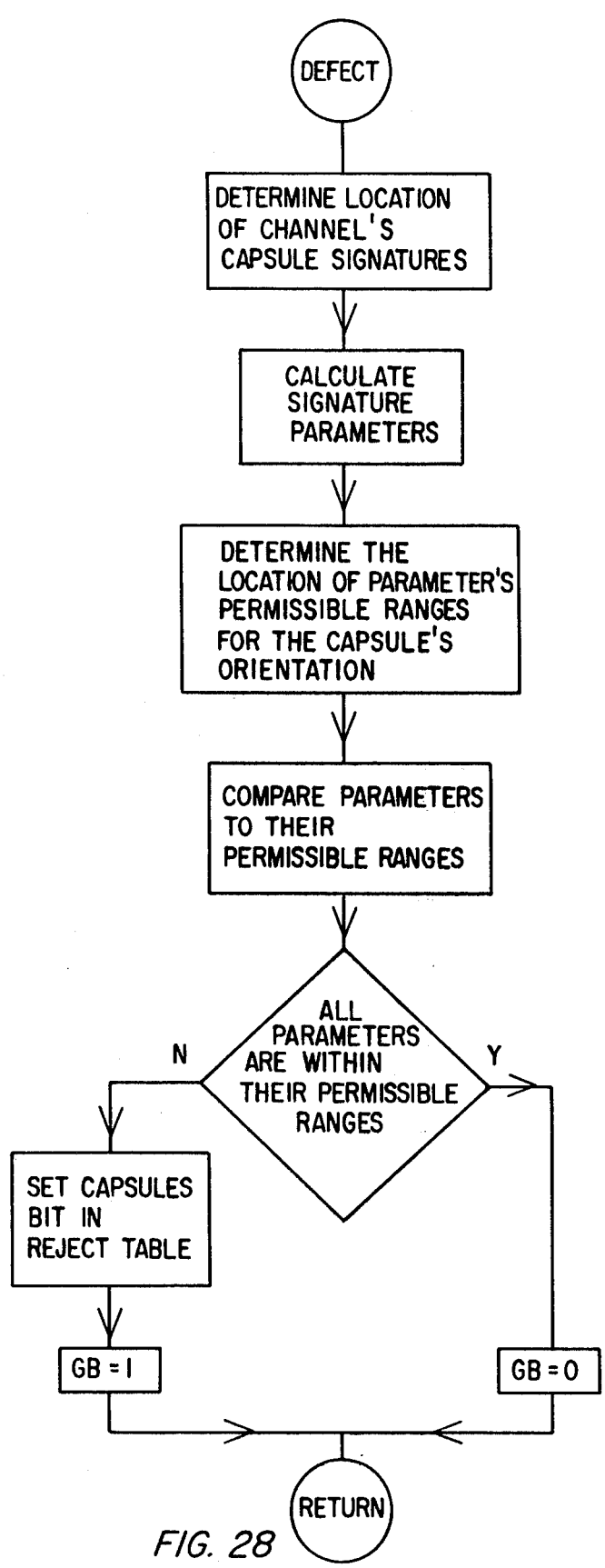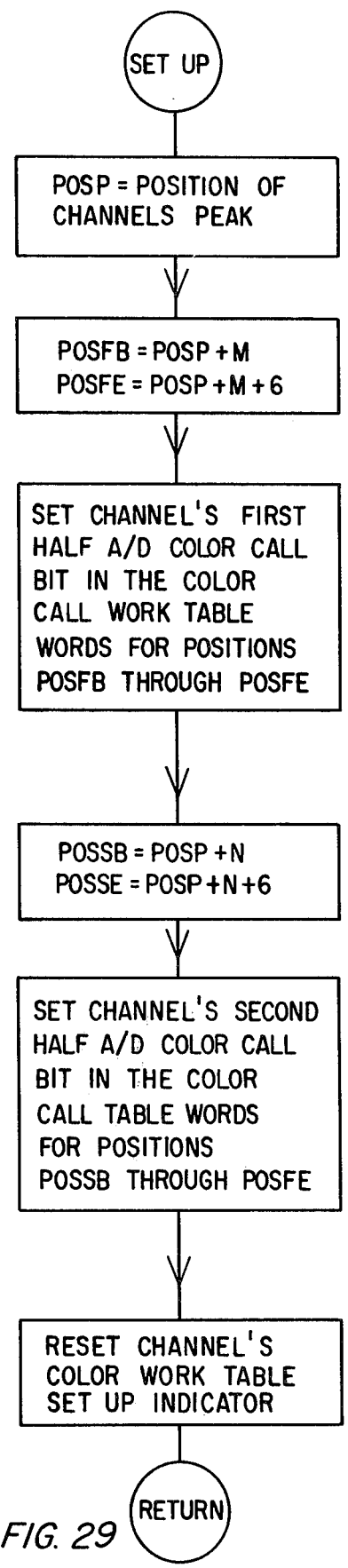
FIG. 28
FIG. 29

METHOD AND APPARATUS FOR COLOR RECOGNITION AND DEFECT DETECTION OF OBJECTS SUCH AS CAPSULES

BACKGROUND OF THE INVENTION

The present invention relates to high-speed, large-volume, automatic and continuous analysis of both the color(s) and shape (geometric form) of discrete solid particular objects such as pharmaceutical capsules. More particularly, the invention relates to the inspection and processing of large numbers of such objects, to identify the existence of and isolate (reject) virtually all "bad" or unacceptable material and to simultaneously provide an accurate running (and ultimately a total) count of the "acceptable" material.

The invention is particularly suited for use in connection with objects which intentionally are multicolored, for example, in a coded or otherwise well defined manner. Although this invention is described by way of example in connection with pharmaceutical capsules, it is to be clearly understood that the principals of this invention as well as the invention itself are applicable to and may be employed in connection with countless different types and kinds of solid discrete particular objects, including solid or multi-colored (including color-coded) objects, such as tablets or color-striped capsules.

In high-speed, large-volume processing, automated monitoring systems have become indispensable in examining the production flow to detect irregularities. Often such systems are intended primarily to replace or supplement present visual inspection methods, and thus they should be capable of achieving at least the same level, and preferably a greater level, of efficiency than that experienced with human inspectors.

Great care has been taken in for example the pharmaceutical industry to clearly delineate between different products for obvious reasons of safety. This is accomplished with various shapes and colors of the dosage forms and containers. Of these characteristics, perhaps the color most readily permits discrimination by the untrained observor having normal perception. Fortunately, the use of color to distinguish dose forms also permits rather accurate automatic machine recognition of a particular dose form. While an arrangement or system for automatic recognition by shape and/or color conceivably can take several different forms, it should be compatible with automatic process control equipment.

With particular reference to medicinal capsules, this widely recognized type of pharmaceutical dosage form is, of course, made in very large quantities. Capsules consist of a cap and body which are telescopically fitted together. Empty capsules are normally supplied assembled to automated filling machines where caps and bodies are disengaged, the bodies filled with medicinal material, and the capsules reassembled. The filled capsules are then subsequently packaged for distribution.

It is, as indicated, of utmost importance that the medicinal material in a capsule can be identified as to type and quantity by external viewing of the capsule. For this purpose, a particular capsule color combination (usually a cap of one color and body of another color) is assigned to each product item manufactured, Also, either prior to or after filling, an identification is printed on the capsules, usually in yet another (third) color.

To preclude improperly identified capsules or improperly filled capsules from entering packages and the like, meticulous inspections are performed on both empty capsules, where the elimination of capsules with imperfections also avoids impairment of the filling machines, and filled capsules.

In most capsule manufacturing installations and, until now, in all capsule filling installations, the aforementioned inspections have been performed visually by human beings. Observers view capsules being conveyed past them by some form of conveying belt, and they manually remove defective or incorrectly colored (e.g. foreign or "double-capped") capsules. The weaknesses in visual inspection are well recognized. Particularly in cases where a relatively large percentage of capsules must be removed, the inspection rate is limited by the operator's removal rate. The observer, moreover, can suffer from fatigue and/or boredom. The inspection effectiveness can reasonably be assumed to be sporadic, since it is dependent upon the inspector's physical and mental state. This visual inspection technique is very costly and sometimes fails to achieve the desired effectiveness. For instance, studies performed in filled capsule production environments indicate that about $\frac{1}{2}$ or $\frac{2}{3}$ of the approximately 0.6% defective capsules are discovered and removed. As to detecting foreign capsules, it is safe to say that the detection probability increases with the apparent color difference(s) between the foreign capsule(s) and the good capsules surrounding same.

It should also be recognized that capsules constitute particularly perplexing objects on which to perform color recognition and defect detection inspections. This is so because capsules are relatively small objects, which because of the great demands therefor must be inspected in large numbers and therefore at high speeds. Capsules, moreover, have highly curved surfaces leaving only very small "stable" portions of the surface thereof from which to obtain legitimate readings (particularly for color recognition). To further complicate matters, capsules have printing thereon which to such a system as this constitutes noise and could lead to the condition of too many "false positive" rejects, simply because the printing may cover as much as one-third of the entire "good" viewing area to the capsule's surface.

In U.S. Pat. No. 3,757,943, issued Sept. 11, 1973, to Chae et al, there is disclosed an invention for the inspection of empty capsules for defects. The invention disclosed in the above-cited patent detects defects by determining unplanned assymmetries in capsules. It does not, for example, have the capability of distinguishing foreign capsules, detecting symmetrical defects, or inspecting filled or printed capsules.

In U.S. Pat. No. 3,737,239, issued June 5, 1973 to Adams and Grimmell, assigned to the Assignee of the present invention, the pertinent subject matter of which is incorporated herein by reference, there is disclosed an invention for inspecting objects including pharmaceutical dose forms to determine whether their color corresponds to a standard. This invention does not particularly deal with detecting defects or inspecting multi-colored objects.

It is desirable to go beyond the disclosed art, and indeed the capsule-related prior art in general, to provide an arrangement capable inter alia of inspecting at a high rate of speed both filled and unfilled (empty) pharmaceutical capsules, both those with and without printing. Furthermore, such an arrangement should be able to inspect multi-colored capsules, particularly those with a single colored cap and possibly a different colored body, for improper color(s) and both symmetrical and non-symmetrical defects.

To be worthwhile, an automatic machine effort should provide a performance capability such that the probability of detection of (1) a foreign (wrong color[s]) capsule should be nearly unity, even where printing is present on the capsule, and (2) any structural defect should be at least 0.7 (which is greater, for example, than the capability of inspectors in a filled capsule inspection line). Moreover, the arrangement should be capable of being easily "set" to accept any specific combination or arrangement of colors, and particularly it should be capable of inspecting the two spherical ends of each capsule for correct curvature. Also, it should be capable of inspecting each capsule near its center region for indications of a chipped or split cap.

SUMMARY OF THE INVENTION

It is an object of this invention to provide an arrangement which overcomes the disadvantages and shortcomings of the prior art and possesses the above-mentioned desirable capabilities.

It is a further and principal objective of this invention to provide a system for inspecting discrete solid particular objects such as medicinal capsules or the like, filled or unfilled, with or without printing, and sorting such material into two main classes, namely good material and bad material, where bad material may be foreign objects (e.g. capsules of an incorrect color scheme), objects of incorrect length or diameter, objects possessing surface defects, or material other than that desired (e.g. having a substantially different geometrical form altogether).

It is another object to provide color recognition and defect detection inspections of small, multicolored, three-dimensional objects moving at high speeds which because of their size and speed provide rather restricted viewing area.

According to the broader aspects of this invention, there is provided an optical and electronic arrangement for inspecting at a high rate of speed large numbers of discrete solid particular objects such as medicinal capsules, with regard to color and/or surface defects, and means associated therewith for rejecting other than good material and for providing a running (and total) count of the acceptable material. Each object (e.g. capsule) is conveyed under at least one of a multiplicity of optical heads, where it is viewed by a multiplicity of sensors. The signals from these sensors are processed by a suitably programmed general purpose computer. The computer controls the means for rejecting material which it determines to be other than "good" material.

The invention is intended to operate in connection with a suitable high-speed transport and feeder mechanism such as apparatus utilized in capsule printing and manufactured, for example by R. W. Hartnett Co.

The objects (capsules) may be loaded into a hopper at the "rear" of the feed and transport apparatus. The feed and transport apparatus locates the capsules for example in one of N holders on a bar of a set of bars which may comprise a transport belt. Thus, N (in the example herein depicted sixteen) separate "channels" of capsules are fed through the machine's transport. As the capsules pass along the transport, they at some point pass under one or more of at least N optical heads (at least one optical head for each capsule channel). While a capsule passes under an optical head, the signals required for its inspection are generated.

Light is brought to an optical head from a source via, for example, one or more fiber optic light guides. Lens systems mounted in the head are focussed on the capsules passing under the head. The optical signals from these lens systems are passed to photodetectors through suitable masks some after passing through optical filters, again, for example, via fiber optic light guides. The photodetectors convert the optical signals to electrical signals which are passed via operational amplifiers to an analog-to-digital conversion system.

In the proposed arrangement there are essentially two optical systems. The first of these is used for color recognition and employs preferably twelve discrete optical channels. These optical channels are operatively divided into four groups of three. The three channels in each group are coupled to one of four photodetectors (e.g. photomultiplier tubes). Each photodetector and its corresponding group of optical channels is associated with a particular color filter and therefore covers a distinct and different region of the visible spectrum, Spatial integration for minimizing the effects of printing on the measured diffuse reflectance of the capsule is accomplished with the three optical channels of each group, coupled to the one photodetector.

The other optical system intended for structural defect detection, employs, for example, two optical channels, and may be an infrared system. This system is sensitive to the specular reflectance of the capsule. Departures from a reference reflectance signature, obtained as the capsule moves past the sensor's optical axis, are utilized for the automatic machine recognition of structural defects.

Since in high-speed situations capsule motion is continuous and the information is acquired "on-the-fly" by the optical systems, this information should be related to capsule position. This is provided by an encoder (e.g. an angular or spatial encoder) arrangement constituting a part of the transport mechanism. This enables data to be taken in connection with specific regions on the capsule.

A computer receives signals from the encoder, the latter being linked specifically to the drive system of the feed and transport apparatus. Through use of the encoder signals, the computer determines which signals from the optical heads to sample at any given time. Then, through control of the analog-to-digital conversion system it samples these signals. From the sampled signals, it constructs for each bar holder of the transport apparatus basically two vectors, comprising the color of the first and the second halves of the material, and signatures representative of the material's shape. The color vectors and shape signatures are then compared with standards to determine if the object viewed is a "good" capsule.

After passing under the optical heads, the transport bar is passed relative to (under) a rejection arrangement which provides rather articulate isolation from the mainstream of those capsules, out of the many being processed simultaneously therewith, determined to be unacceptable. The rejection arrangement comprises a corresponding number N (again, in the example given sixteen) of reject air jets controlled by the computer via for instance solenoid valves. As each transport bar passes under the reject arragement or head, the computer causes the air jets corresponding to the bar's capsule holders which do not contain good capsules to fire.

An air stream from a fired jet moves the material in its corresponding capsule holder out of the holder and into a slot in the bar from where it is carried under the remainder of the regular transport path. Good capsules remain in their holders until they reach the "front end" of the transport apparatus where they emerge from their holders to be received for example into a collecting bin.

The computer keeps track of the number of good capsules passed through the transport mechanism, displays the count, updating the display for example with each additional thousand good capsules, and, at the end of the inspection run, prints out the number of good capsules passed.

Standards (as to which dose forms [capsules] under investigation will be compared) are achieved (and eventually incorporated into the computer's inspection program) through quantitative evaluation of various examples of "good" forms by, for example, running said "good" forms through the system and having the computer under control of a suitable program find, store and subsequently display distributions of the measured parameters of these "good" forms.

The present invention has been developed to automatically determine whether the color of a sample is, by some reasonable criteria, sufficiently close to a standard color, where the standard color (e.g. a four-dimensional vector) and the "sufficient closeness measure" may be determined from certain of said distributions related to color.

It is pointed out here that the reference or standard that is eventually incorporated into the program preferably is available in a form which may be periodically updated by the computer through averaging the readings derived over say the previous two hundred good capsules passed through a sensor head.

In the second optical system, i.e. for defect detection, which is sensitive to the specular reflectance of the object under observation, use is also made of a reference, in this case a reference reflectance signature. Departures, as measured by failures of parameters of the observed signature, as the capsule moves passed the optical sensors, to be sufficiently close to the parameter values of the reference, are utilized for the machine recognition of such defects as dents, punched ends, chips, splits, etc. Said parameter values of the reference and the required closeness to those values is determined from the above-described parameter distributions.

Among the numerous noteworthy features and advantages of this invention, it is emphasized that the capability now exists for: detecting virtually all improperly colored material and most material with shape defects, at a rate for example of up to 800,000 units per hour; and 100% inspection of throughput. The invention may be employed with regard to objects of virtually any color combination (or coding) and shape, so long as the object's shape (i.e. a standard of that object's shape) and the desired color arrangement are known. It will be readily apparent that apparatus in accordance with the invention may be utilized as a sorting machine.

It is to be particularly noted that this invention provides accurate color recognition and defect detection even in cases where substantial printing, usually of an altogether different color, is to be found on the object. Moreover, a system according to the invention is capable of alarming for and rejecting each unacceptable object and even at the extremely high speeds recited above.

In specific regard to defect detection of capsules, the invention provides detection of such structural defects as dents (especially punched or dented ends), dings (abrasions), "splits" (e.g. cap splits where the body color shows above part of the cap), chips, double caps, lost bodies or caps and short (or long) bodies and caps. It has been confirmed that apparatus according to the invention indeed rejects less than 1% of good capsules, detects greater than 99.9% of all capsules having improper color, and rejects at least 70% of all structural defects including better than 90% of all indentations of significant magnitude. In regard to the latter consideration, it should be pointed out that the relative severity of the "structural defect" plays an important part in detection. It will be appreciated, for example, that minute dents and abrasions which contribute very substantially to the totality of instances of structural defects missed by the apparatus, probably go largely unnoticed; however, such minute "defects" in the largest part pose no particular hazard or problem, even, for example, to automated apparatus for filling capsules.

Ideally, since capsule orientation is a most important factor in defect detection capability, the capsules should be fed in a way where virtually the entire periphery of each capsule can be viewed by the inspection sensors. The present invention approaches the ideal by providing an arrangement which enables at least two viewings of each capsule moving perpendicular to its axis of symmetry and being "flipped over" in between said viewings, as well as the above-mentioned at least one viewing of each capsule moving parallel to its axis of symmetry. Moreover, it is within the scope of this invention to utilize a transparent (plastic) transport mechanism to enable "underneath" viewing of the capsules as they move along the transport mechanism and employing, for example, transmittance inspection techniques, as opposed to the reflectance techniques considered above.

BRIEF DESCRIPTION OF THE DRAWINGS

The above-mentioned and other objects and features of this invention will become more apparent and the invention itself will be best understood by reference to the following description taken in conjunction with the accompanying drawings in which:

FIG. 15 is a partially schematic diagram of the reject mechanism of FIG. 1;

FIG. 16 is an enlarged perspective view of a portion of the transport of FIG. 1 showing the position of rejected capsules as acted upon by the arrangement of FIG. 15;

FIGS. 25-30 are flow diagrams illustrating the non-interrupt level software, comprising an executive (FIGS. 25-26), two evaluation subroutines (FIGS. 27-28), a color work table setup subroutine (FIG. 29) and a calibration subroutine (FIG. 30);

DESCRIPTION OF THE PREFERRED EMBODIMENT(S)

Figure 1:
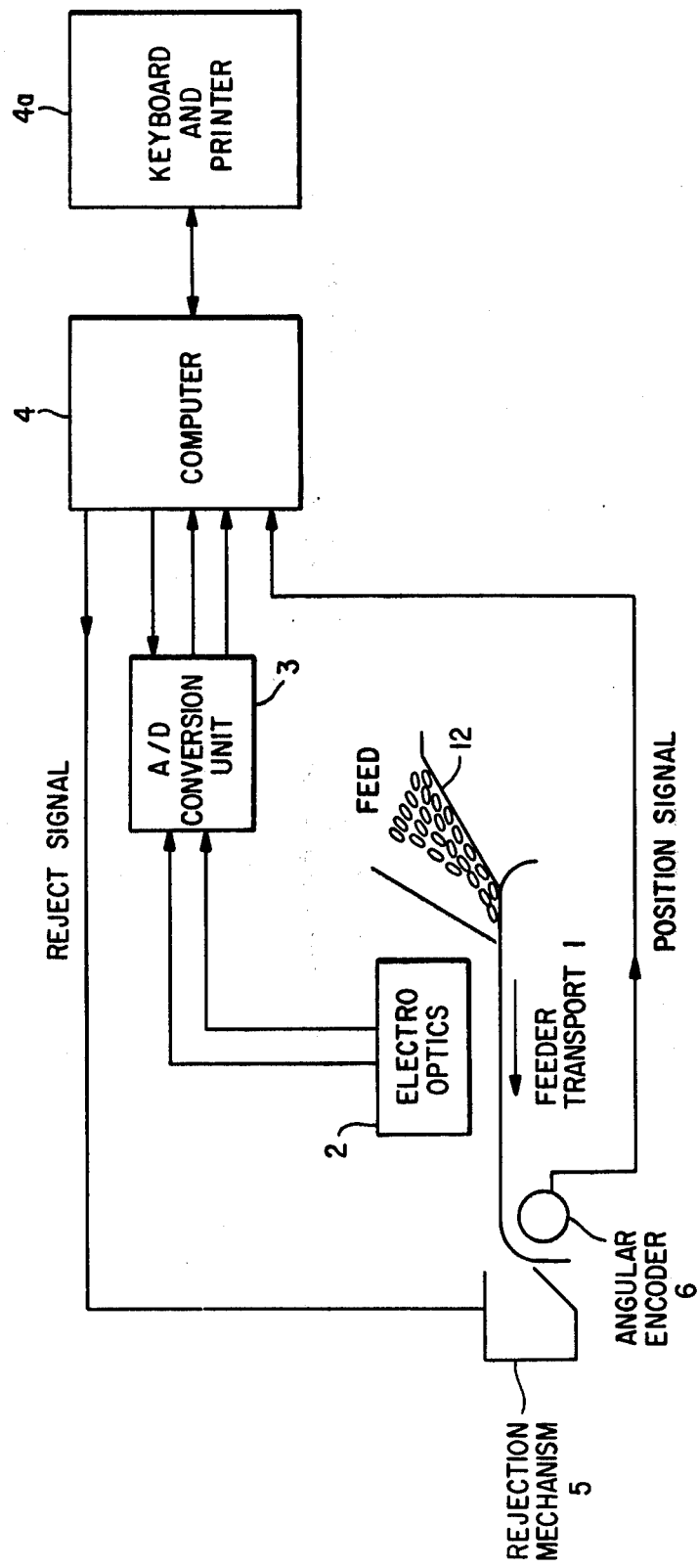
FIG. 1 is a schematic diagram illustrating the major systems comprising an arrangement in accordance with the invention.

With reference to FIG. 1, the invention is comprised of the following major systems: a feeding and transporting mechanism 1, including an angular encoder 6, which mechanism may take the form of a modified feeding and transporting mechanism from a high-speed capsule printing machine such as that manufactured by the R. W. Hartnett Company; an electro-optics system 2, including an array of optical sensor heads; a data acquisition and processing system, including an analog-to-digital conversion arrangement 3 and computer 4; and a rejection mechanism 5.

Figure 2:
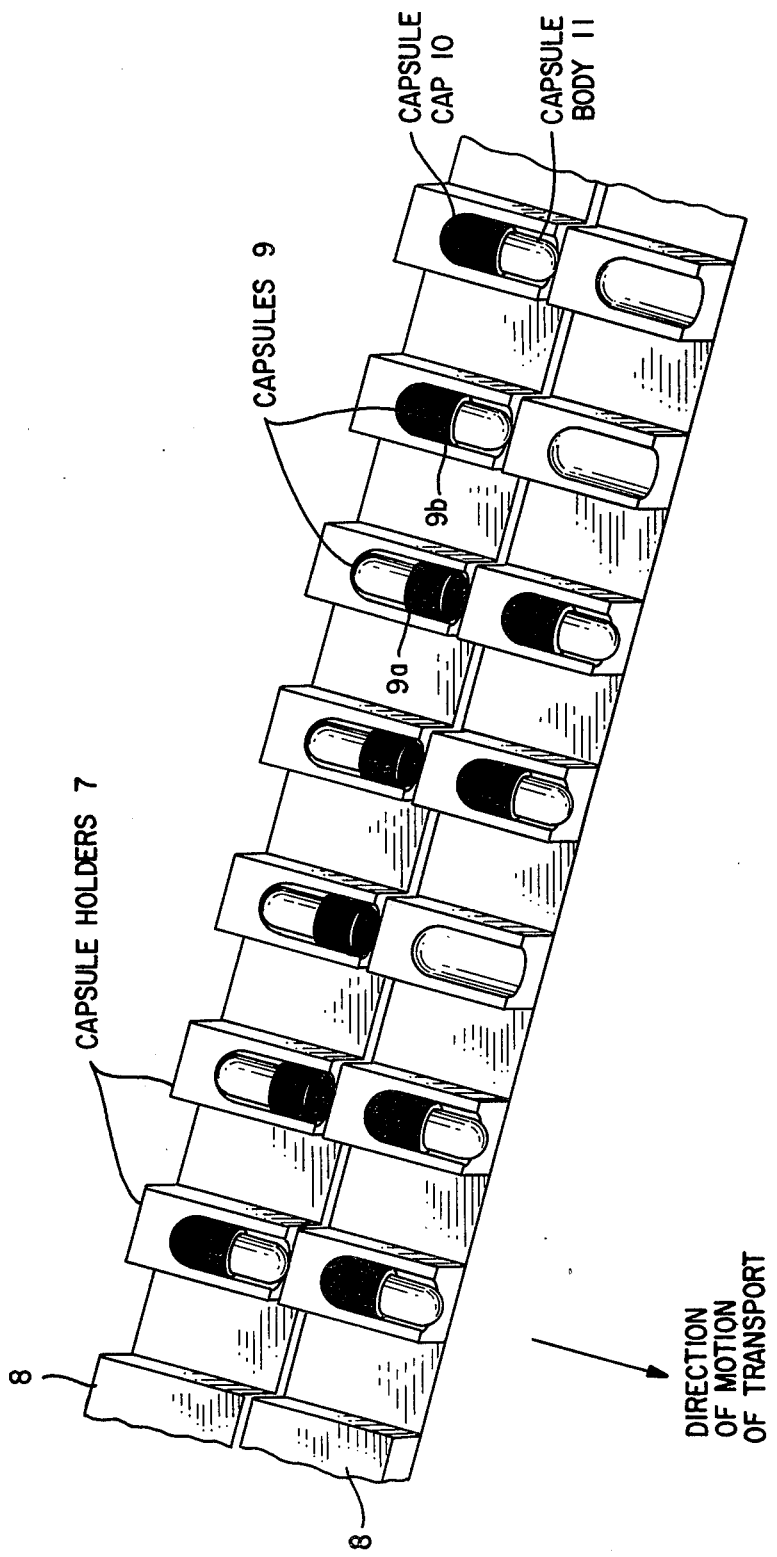
FIG. 2 is an enlarged perspective view of a portion of a preferred embodiment of the transport system of FIG. 1.

Capsules are placed in a hopper (not particularly shown in FIG. 1) from which via a feeder 12 they are derandomized and emerge (with reference to FIG. 2) in holders 7 of transport bars 8 making up part of the transport means. It should be pointed out that the geometry of the transport mechanism largely dictates the specifics of the optical arrangement used.

Each of the capsules 9 (FIG. 2) normally consists of a cap 10 and a body 11 which are telescopically fitted together. The capsules 9 as they emerge from the feeder 12 are, in this example embodiment, aligned with their symmetrical axes parallel to the direction of motion of the holders 7. Some capsules will have their respective caps 10 at the front end of their holders 7 relative to the direction of movement, such as capsule 9a in FIG. 2. Others will have their bodies at the front end of their holders 7, like capsule 9b in FIG. 2. The multiple number of holders 7 per bar 8 causes a multiple number of streams or flow channels of capsules to be transported from the feeder 12.

Apart from the references or standards comprising part of the computer's programming, the region of the capsule holders behind the capsules 9 may have thereon white standards of reflectance. By this, for example, the voltage obtained from the photodetector device as the standard passes under the sensor head could be used as a reference voltage. This would for instance enable compensating for "drift" in the photodetecting device.

A plate (not particularly shown in FIGS. 1 and 2) is mounted on the frame of the transport, and optical heads, at least one head for each capsule flow channel (see FIGS. 3 and 5), are mounted on the plate. As a capsule moves along the transport 1 of FIG. 1 it at some point passes under an optical head of the electro-optics subsystem 2.

Figure 3:
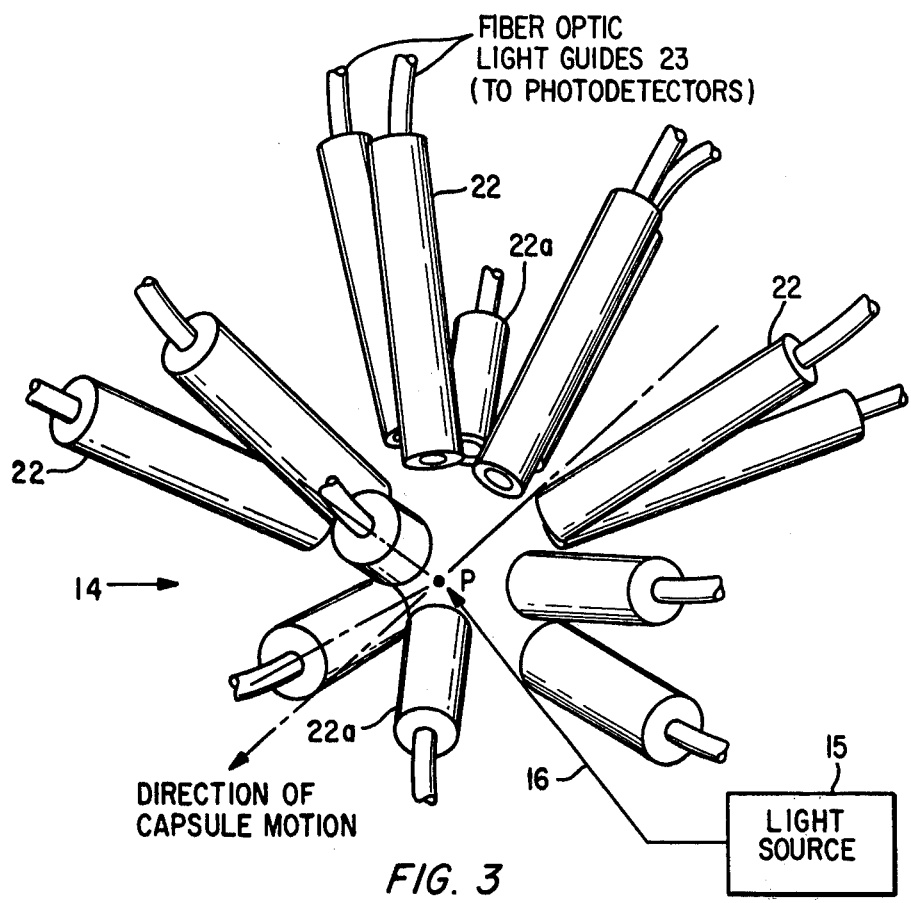
FIG. 3 is a diagrammatic illustration of the arrangement of optical channels of an optical sensing head comprising part of the electro-optics system of FIG. 1.

With reference to FIG. 3, as each capsule passes under the optical head 14, it is illuminated by a (schematically illustrated) broad band light source 15, for example, a commercially available Xenon lamp (such as an XBO-150, manufactured by Osram Inc.). Light may be conducted from the source 15 to the optical head 14 via conventional fiber optic guides, schematically represented in FIG. 4 by the line/arrow 16. The illuminated portion of the capsule is viewed by a multiplicity of sensor channels 22, whose outputs are conducted via fiber optic light guides 23 to photodetectors (see e.g. FIG. 7).

More particularly, the illustration in FIG. 3 of optical head 14 comprises fourteen discrete optical channels, which may be thought of as being comprised of two subgroups of twelve and two optical channels each. The one subgroup of twelve optical channels is associated with the color recognition aspects of the present invention whereas the two-channel subgroup (i.e. optical channels 22a in FIG. 3) is associated with the defect detection aspects of the present invention.

Figure 5:
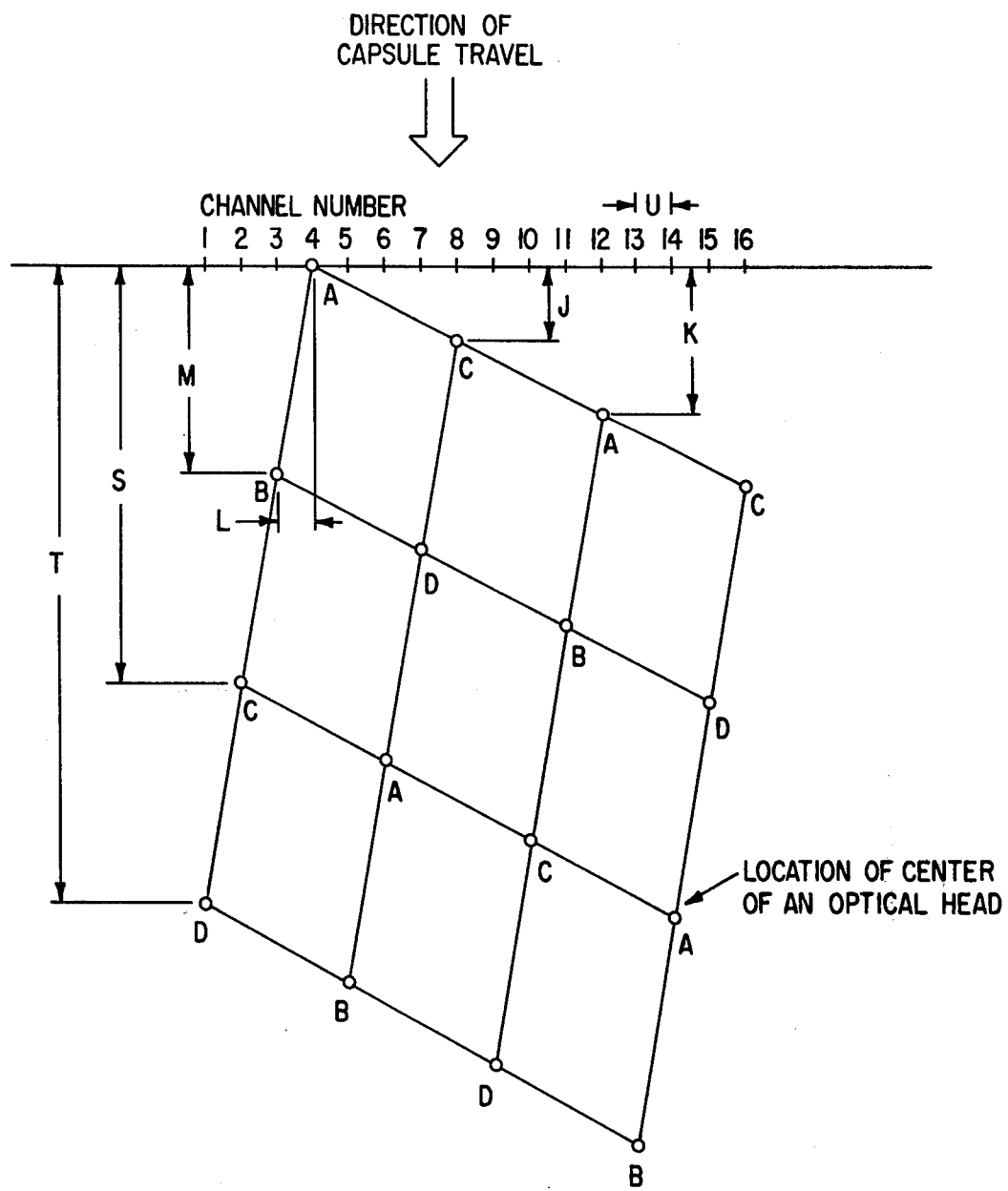
FIG. 5 is an illustration showing a preferred arrangement of a number of optical heads relative to the flow channels of the objects undergoing inspection.

The sixteen optical sensor heads 14, corresponding to the sixteen flow channels of the transport subsystem, may be arranged in the array shown in FIG. 5 relative to the flat region of the transport subsystem. The particular array shown and its location above the flat portion of the transport mechanism is helpful for proper timing and sequencing of data collection with the arrival of capsules.

Figure 4:
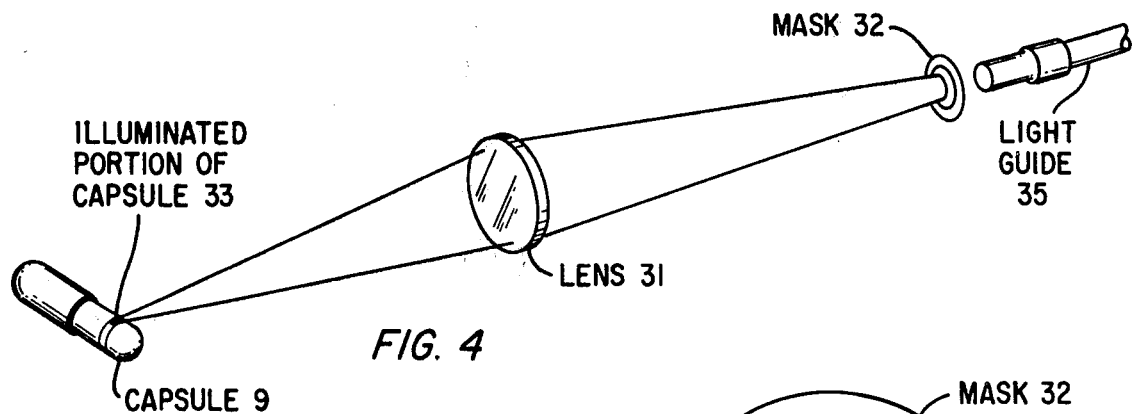
FIG. 4 is a largely schematic exploded view of the components and function of certain ones of the optical channels of FIG. 3.
Figure 4A:
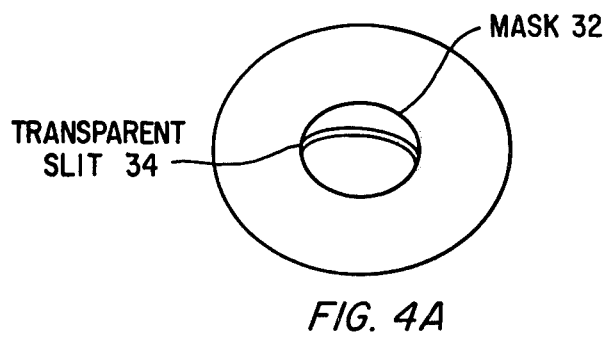
FIG. 4A is an enlarged view of a preferred embodiment of the mask of FIG. 4.

With reference to FIG. 4, each optical channel provided by each optical head 14 consists of a lens 31 and a mask or spatial filter 32. The lens 31 focuses an image of the illuminated portion or segment 33 of the capsule 9 onto the mask 32. The mask 32 is of the type which is opaque except for a slit 34 (see enlargement illustrated in FIG. 4A) which is shaped and arranged such that essentially only light reflected from a segment of the capsule surface is transmitted through the mask onto the termination of a fiber optic light guide 35. For good results, it has been found advantageous to have the segment viewed (image of elliptical slit) amounting generally to about 1/6 the capsule circumference. In each optical channel, however, the lens 31 and slit 34 can be and preferably are chosen so as to optimize the discrimination of some significant capsule features. The elliptical slit shown ensures inter alia sufficient resolution of the boundary between the cap and body of a capsule, and readily enables observation of features on the "cylindrical" portion of the capsule, particularly for color recognition. On the other hand, the masks utilized in the optical channels for defect detection preferably have linear slits, to particularly observe the slope changes at the capsule ends. It will be appreciated that other shapes and kinds of masks may be adopted to serve the intended purposes, for example, a grid of openings in place of the slit. It will also be appreciated that the masks may well be different for different kinds of objects, in view of the desire to highlight certain features of the objects under consideration. A desirable geometry of the elliptical slit would have the major and minor axes and the segment length provided thereby defined by: (1) the angle between the optical axis and the capsule axis; (2) the capsule segment viewed by each channel; and (3) the magnification (if any) of the capsule image.

The optical channels of the optical head(s) 14 (utilized for color recognition) for a capsule stream or flow channel are grouped (FIG. 7), three to a group, with one photodetector 45 being provided for each group of optical channels 41 at the other terminus of the fiber optic light guides 42. Each group of three sensors (optical channels) serves as a spatial integrator and covers one of the four spectral domains selected in the visible region of the spectrum, said domain being established by optical filter 44.

Figures 7, 7A:
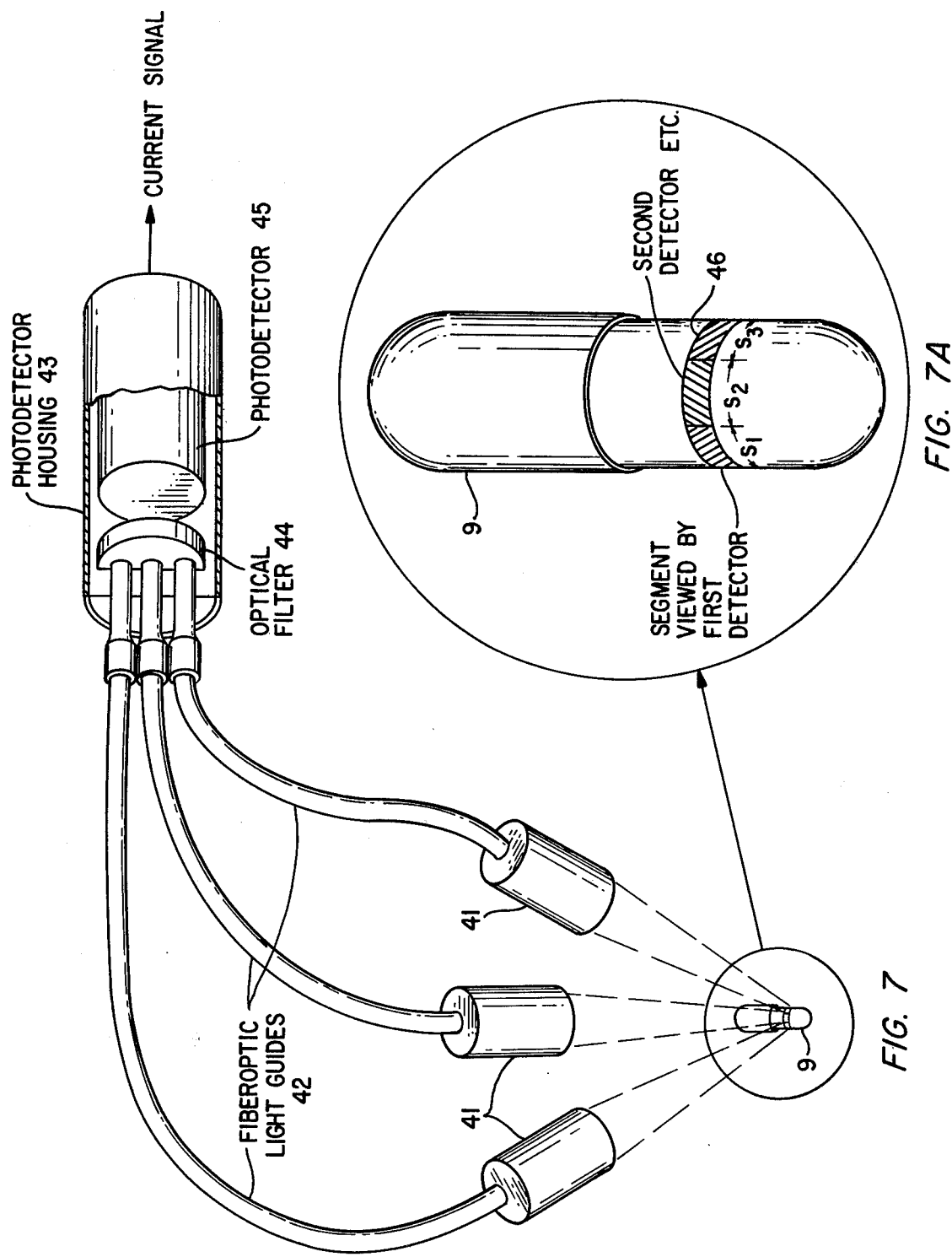
FIG. 7 and FIG. 7A illustrate a portion of the electro-optics system of FIG. 1 related to color recognition.

Each optical channel of a group views a different segment of the illuminated portion of the capsule. In the illustration of FIG. 7 it is particularly seen that the optical channels may be arranged to view contiguous segments $S_1$-$S_3$ of the capsule 9, comprising a total illuminated portion 46. One main purpose in this, of course, is to provide for this (and each such) group enough different views of the capsule disc to enable any printing encountered to be disregarded.

In FIG. 7, the signals from the optical channels 41 of a group are transmitted via fiber optic guides 42 to the photodetector 45 having housing 43. The optical signals of the group may then pass through the common optical filter 44 (each group having associated therewith a unique and different optical filter 44), and their resultant filtered signal, i.e. the spectrally resolved light, impinges upon the photodetector 45, which may, for example, be a commercially available photomultiplier (such as an RCA 6217 or 931A) tube. The photodetector 45 converts its optical signal to a proportional electric current which represents a spectral component of the spatially integrated image of the combined capsule segments $S_1$-$S_3$ viewed by the optical channels 41. Thus, in this example four current signals are generated for each of the sixteen optical sensor heads for the purpose of color discrimination.

Figure 8:
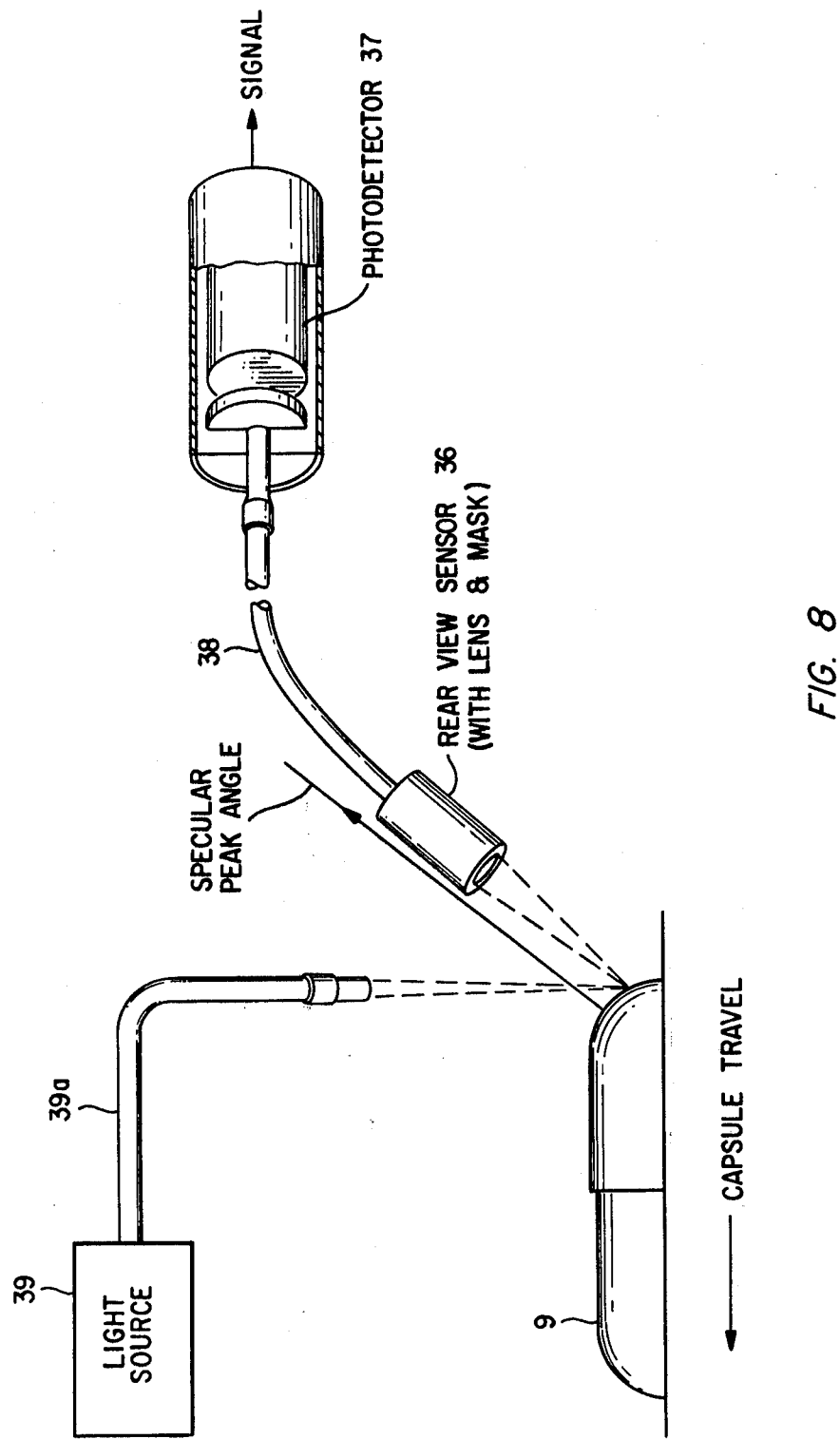
FIG. 8 illustrates a portion of the electro-optics system of FIG. 1 related to defect detection.

In reference to FIG. 8, an optical channel for defect detection is depicted as comprising (like the color recognition optical channels) a sensor 36 with a lens and a mask. The defect detection optical channel shown is the "rear view" channel. Virtually an identical sensor/light guide/photodetector arrangement is provided for the "front" view (relative to the direction of capsule travel). Each of these two optical channels for defect detection (elements 22a of FIG. 3) are positioned to make specular reflectance measurements (e.g. in the infrared) which can be related to the presence of surface imperfections. The photodetector 37 associated with each such optical channel, and in communication therewith via light guide 38, makes use of the lens and mask arrangement of the sensor 36 to monitor the intensity and temporal relationship of the specular peak derived from light reflecting off the capsule 9 as provided by a source 39 via light guide 39a. Typically this peak occurs as the cone of light shown in FIG. 8 rotates about an axis substantially normal to capsule motion. If an end dent exists, the unique signature of the capsule shape is lost, possibly including the specular peak resulting from a unique point of which the condition of the angle of incidence equalling the angle of reflection occurs. Defect detection, then, is observing the "plotted" waveform of sampled points in time for the various characteristics that should be there. Deviations from expectations of one or more of these main characteristics (detailed hereinafter) constitutes a defective capsule, and a reject signal will be generated. It should be pointed out that if desired an internal record could be kept by the computer (and printed out at the end of an inspection, for example) as to which or how many reject signals resulted from foreign capsules and which or how many from structural defects. There may also be provided a separate reject signal for each and a separate reject channel for each as well.

Figure 9:
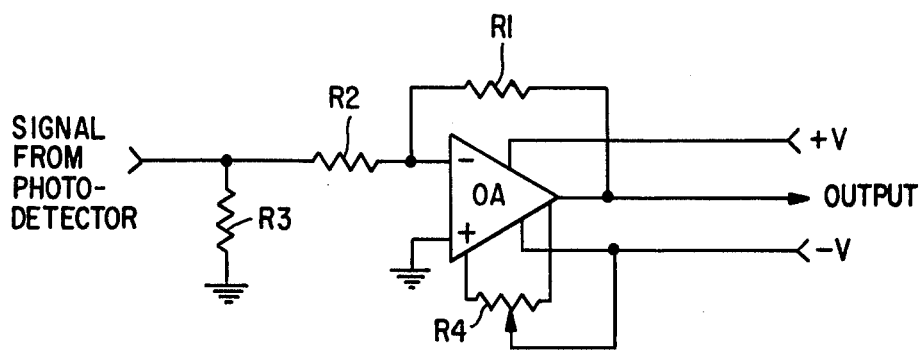
FIG. 9 is a schematic diagram of a circuit for providing a preferential conversion of the output of the photodetector of FIGS. 7 or 8.

The electrical current output from each photodetector (45, 37) is converted to a proportional voltage. With reference to FIG. 9, the current output from a photodetector is fed to a circuit such as that shown, where this current is divided, with part passing to ground through resistor R3 and part passing through resistors R2 and R1. Through the action of differential amplifier OA, an output voltage proportional to the current passing through R2 and hence proportional to the photodetector output current is generated.

Figure 10:
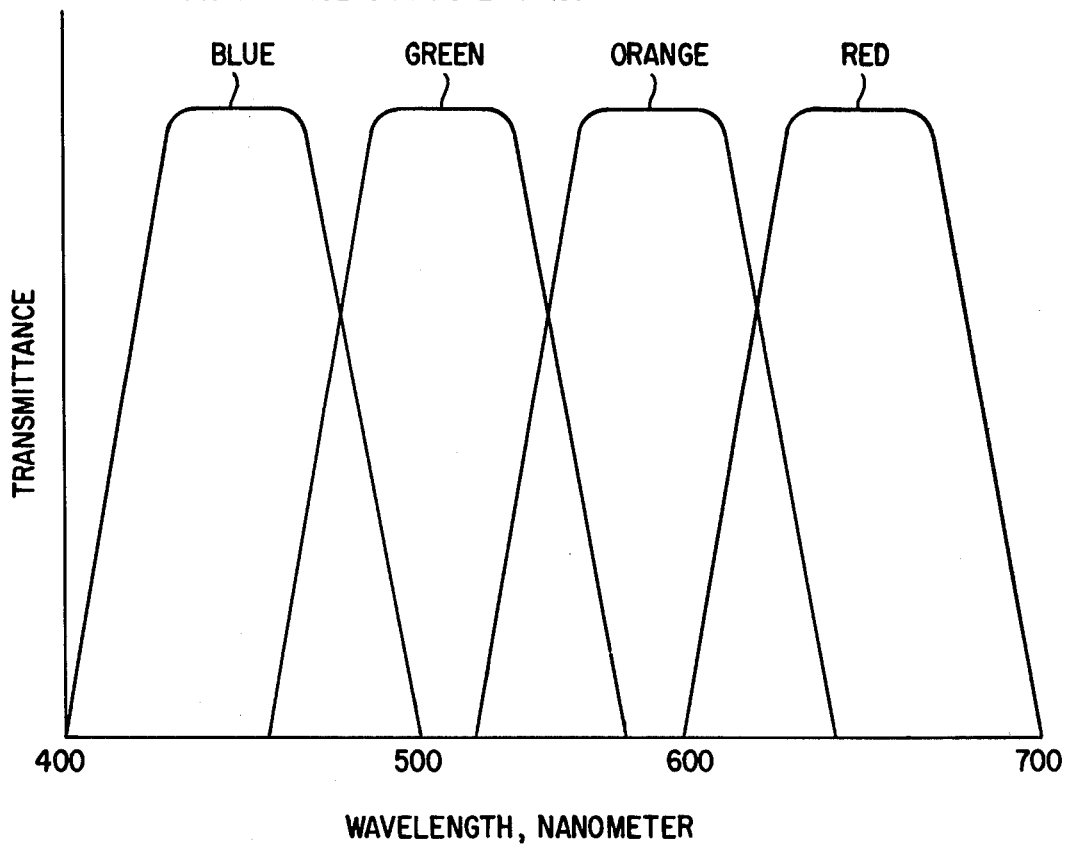
FIG. 10 is a graphical representation of preferred operative ranges of the color filters associated with respective ones of the photodetectors utilized for color recognition.

The signals from an subset (four in the example here described) of the set of photodetectors (total of six, with one photodetector associated with each of the defect detection optical channels) associated with an optical head are used for color determination. As alluded to above, optical filters preceeding each of these photodetectors have different transmittance characteristics with pass bands in the visible portion of the optical spectrum. Commercially available filters (for example Baird Atomic 14-83-68 Type B-5, 4380A; 14-83-95 Type B, 5120A; 14-83-95 Type B, 5880A; and 14-83-95 Type B, 6620A filters) which approximate the ideal curves of FIG. 10 are used. Obviously, say for a blue capsule half, a high match would result for the blue filter and a high signal output from its associated photodetector would result. The other filters would cause correspondingly lesser signals output from their photodetectors. Thus, the outputs of this subset of photodetectors associated with an optical head may be thought of as components of a vector representing the color of the viewed segments of an object (capsule).

Because the photodetecting devices and/or light sources used may be subject to drift, periodic calibration of the system is advisable. It is proposed to accomplish this, for example, by having the computer determine for each capsule channel the average of the readings for say the previous 200 good capsules, in accordance with standard programming techniques, and update the initially stored reference (standard) information thereby. Also a calibration prior to an inspection may be made in this manner as will be clear from the software description hereinafter. Another technique for accomplishing essentially the same end may (as alluded to hereinbefore) involve mounting a white standard of reflectance on each channelled feedbar, just behind the capsule channel. The voltage obtained from the photodetector as the standard passes under the sensor head could be used as a reference voltage. The data from the immediately preceeding capsule may then be compared with it.

The electro-optical subsystem 2 (FIG. 1) produces, then, from each optical head thereof, a set of analog electrical outputs, (in this example a set of six voltages), in the above-described manner. A subset of each such set of electrical outputs is utilized in the creation of a color vector (in this case a four dimensional vector). As these outputs (ninety-six, where sixteen optical heads for sixteen channels are used and six electrical outputs are associated with each head of the electro-optics subsystem) are analog signals which are to be converted to digital signals, all are connected to the analog-to-digital (A/D) conversion system 3 (FIG. 1). The converted signals are then stored in the computer and acted upon.

The A/D system 3 used may be any suitable commercially available unit, for example, the GMAD-2 unit manufactured by the Preston Scientific Corporation.

Figure 11:
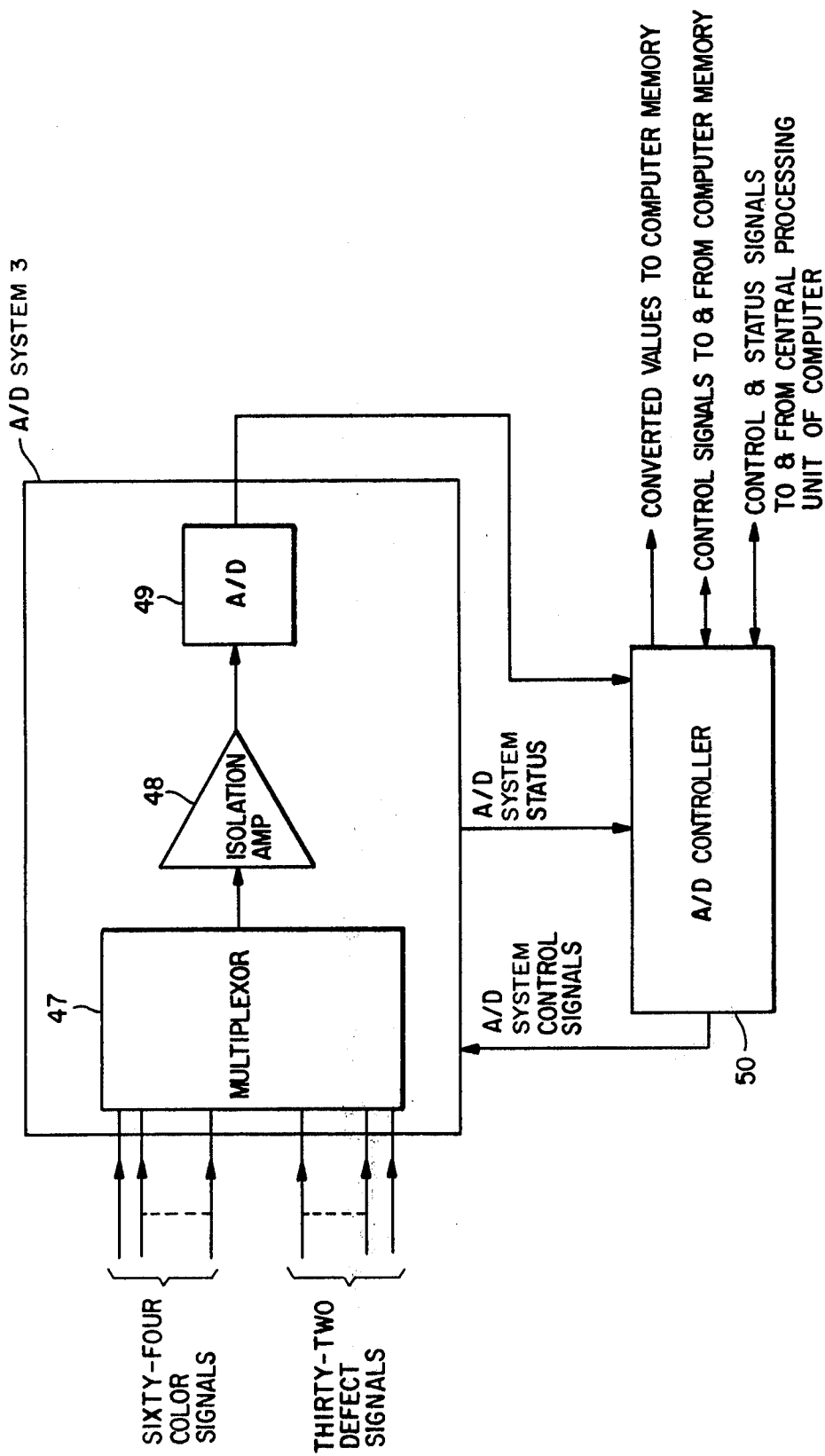
FIG. 11 is a schematic block diagram of the A/D conversion unit of FIG. 1.

The hardware for performing the analog-to-digital conversions, i.e., the A/D subsystem, may be thought of in terms of an interface unit, such as that depicted in FIG. 11, which comprises a multiplexer 47, an isolation amplifier arrangement 48 connected to the multiplexer 47, and an analog-to-digital (A/D) converter 49 connected to the isolation amplifier. Also shown in FIG. 11 is a controller arrangement 50 connected to the A/D system 3 via A/D system control signals lines, an A/D system status line and output lines from A/D converter 49. As shown in FIG. 11, control and status signals pass over lines interconnecting the controller 50 with the computer's central processing unit. Also, the converted signals values from the A/D subsystem are passed through controller 50 to the computer's memory. Lastly, control signals pass over a line interconnecting the controller with the computer memory.

The multiplexer 47 receives as input the 96 analog signals (sixty-four for color recognition and 32 for defect detection). On command from the controller 50, the multiplexer, in this example of embodiment, connects one (and only one) of these inputs to its output. This output is connected to the input of isolation amplifier 48.

Multiplexer arrangement 47 may be any suitable arrangement well known to those skilled in the art. The multiplexer output is passed through the isolation amplifier to be converted in the A/D converter to a digital number and then passed on to the controller 50.

The inputs to the A/D converter 49, of course, are individual voltage levels, as provided, for example, by the circuitry of FIG. 9. The output of the A/D converter is a set of bits (ones or zeros). When the A/D converter 49 reaches a steady state, the binary value of the output is proportional to the analog input voltage. Actual digital values corresponding to the various analog inputs may be established through a suitable table. The number of bits of the A/D 49 output (in the example case here depicted a ten-bit output) may be selected for the desired percentage of resulution.

The controller 50 communicates with the computer control processing unit (CPU) and controls the actions of the multiplexer 47, the isolation amplifier 48 and the A/D converter 49. For each set of required analog-to-digital conversions the controller receives the following information from the computer's CPU:

(1) The starting multiplexer address (MUX) for the set of conversions.
(2) The number of analog-to-digital conversions to be made.
(3) An indication of the function to be performed with the converted values (either storage of each converted value in the computer's memory or storage of the sum of the converted value and a value already in the computer's memory).
(4) The starting location of a set of locations in the computer memory where the converted values (or sums of the converted values and the values in those locations) are to be stored. It then goes through the following sequence of operation for each point to be converted. The controller through signals to the A/D conversion system causes the multiplexer 47 to connect the required input to the amplifier 48. The controller then by monitoring the A/D subsystem "busy" line determines when the A/D converter 49 has settled to a steady state, and finally, causes the A/D output (or the sum of the output and a previously stored value) to be written into the computer memory location. After each set of conversions, the controller determines if it has received commands for more sets of conversions. If it has it initiates the first of these. Upon initiating the first conversion of any set of called-for conversions the controller checks if it has received further commands for sets of conversions. If it has not it interrupts the activities of the computer so as to inform it that all calls for sets of conversions have been completed or initiated.

Figure 11A:
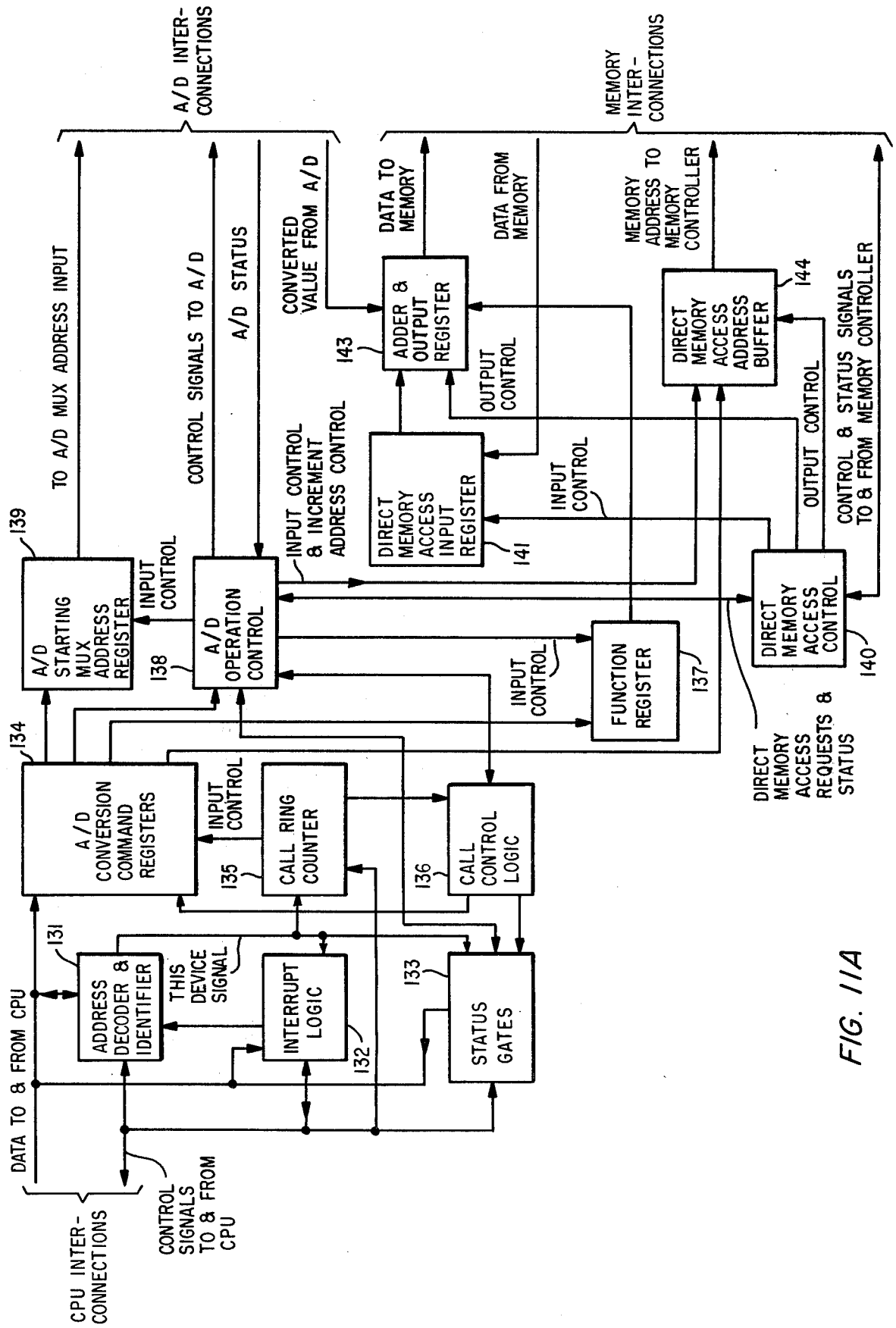
FIG. 11A is a schematic block diagram of the A/D controller of FIG. 11.

FIG. 11A is a block diagram comprising an arrangement of the A/D controller used in the preferred embodiment. With reference to that figure, the controller is indicated as being connected to the following:

1. the computer's central processing unit;
2. the computer's memory and
3. the analog-to-digital conversion subsystem. Command for A/D conversions are issued by the central processing unit by "writing" three words to the controller. The first word contains a computer memory address, the second an A/D multiplexer address and the third a number of conversions and a function indicator. These commands are gated into proper positions in a set of four A/D Conversion Command Registers 134 by a Call Control Ring Counter 135. The Call Control Logic 136 advances the command to the highest command register. When the A/D operation control 138 is not busy the call control logic 136 signals it to begin the A/D operation.

The A/D operation control 138 then gates data from the command in the highest register of the A/D conversion command registers 134 into the direct memory access (DMA) address buffer 144, the A/D starting MUX address register 139, the function register 137 and its internal number of conversions register. The A/D operation control 138, indicates to the call control logic 136 that it has fetched an A/D command and is now busy (which causes all calls still in the A/D conversion command register 138 to be advanced one register), signals the A/D subsystem to convert the value input to the multiplexer at the address on the A/D MUX address lines (in the A/D starting MUX address register 139) and signals the DMA control 140 to fetch a value from memory. The DMA control 140 then signals the computer's memory controller that it wants service. When signalled by the memory controller the DMA control 140 places the contents of the DMA address buffer 144 on the memory address lines to the memory controller, signals the memory controller it wants to read the contents of the addressed memory location and sets up the DMA input register 141 to read a pulsed value of the addressed memory location from lines from memory. On a signal from the memory controller the DMA control 140 disables all signals to the memory controller and signals the A/D operation control 138 tha the read is complete.

The A/D operation control 138 monitors the A/D subsystem status. When it finds that both the requested A/D conversion and the requested memory read are complete it signals the DMA control 140 to write a value into memory. The DMA's interaction with the memory control is the same as for the fetch described above, except it signals for a "write" to the addressed memory location instead of a read, and it places the contents of the Adder and output register 143 on the data lines to memory rather than setting up to read data from memory. The value output to memory depends on the value in the function register 137. If the function register value calls for an add, the value to memory is the sum of the A/D output and the value read from memory. Otherwise it is just the A/D output. Upon completion of the write the DMA control 140 signals the A/D operation control 138.

When the A/D operation control 138 determines that the write to memory is complete it advances the value in the DMA address buffer 144, decrements its number of conversions register and determines if all conversions for the A/D command being processed have been made. If it determines that all conversions have not been made it signals the A/D subsystem to convert the value input at the next sequential multiplexer address from the value which the previous conversion was made and signals the DMA control 140 for a read. Handling of this conversion is then exactly as described above. If after receiving a write complete signal A/D operation control 138 finds that all the conversions for the A/D command have been completed, it signals the call control logic 136 that it is no longer busy.

The computer CPU can determine the A/D controller's status at any time by issuing a status request output to the controller. This will cause the status gates 133 to gate values of signals including the "A/D operation control busy", "A/D conversion registers full", and "A/D conversion registers empty" signals to the CPU at times called for by control signals from the CPU.

The A/D controller may be set up to interrupt the CPU under certain circumstances. This is done by outputting a "command" output to the controller specifying the interrupt conditions. The possible conditions include: A/D conversion command registers not full and A/D conversion command registers empty. The interrupt conditions are stored in the Interrupt Logic 132. This logic when it detects an interrupt condition raises an interrupt signal to the CPU. On receiving an acknowledgement from the CPU it causes the address decoder and identifier 131 to place the A/D controller's device address on the data lines to the CPU while the acknowledgement signal is active.

Control signal lines and data signal lines to the CPU are connected (with the exception of the interrupt acknowledge line) to other circuit boards in the computer as well as to the controller.

Thus, when instructions from the CPU are issued on these lines the controller must determine if these instructions are for it. This function is performed by the address decoder and identifier 131 which determines from the instructions device address whether the instruction is for the A/D controller. When the instruction is for the controller, this circuitry signals the Interrupt Logic 132, status gates 133 and call ring counter 135 so the proper hardware will respond to the instruction.

The signal(s) to be converted at any time by the A/D subsystem is (are) selected (determined) by the computer 4 (FIG. 1) which may be a commercially available computer (such as the Model 80 minicomputer with 32kB of memory and a Universal interface module (UIM) manufactured by Interdata Corporation), and carried out under the controller's supervision. As stated, on completion of the A/D conversion of a selected signal, the digital number representing the converted signal (or the sum of that number and a number in memory) is read into the computer 4.

The computer 4 determines when to read (via the A/D controller and A/D system) given signals through information received from the angular encoder 6 (such information is being input to the UIM board in the computer) attached to the transport mechanism 1 and through an internal algorithm which operates on read data.

By choosing to "read" certain electro-optics subsystem outputs at particular times the computer is able to obtain the data necessary to construct color vectors of the cap and body and shape signatures of each capsule passing under the optical heads of the electro-optics subsystem 2.

Figure 12:
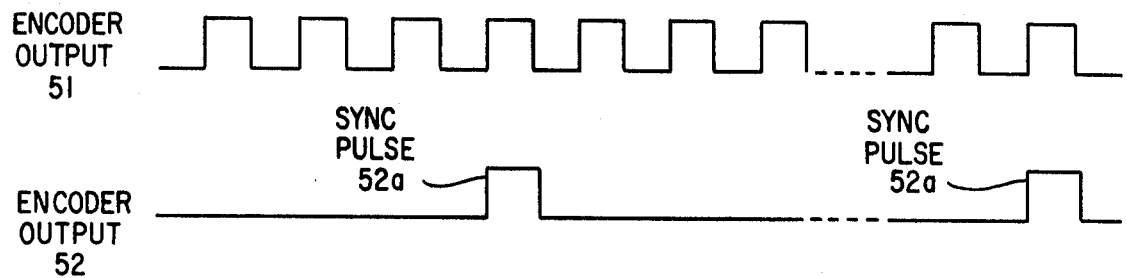
FIG. 12 illustrates, relative to time, signals output from the encoder of FIG. 1.

With reference to FIG. 12, the angular encoder 6 (FIG. 1), which may be a commercially available unit (e.g. a Baldwin Model 5V277a), produces two output signals, one preferably being a square wave 51, and the other signal, i.e. 52, comprising a pulse 52a referred to as a "sync" pulse, which occurs every set number (3,600) of cycles of the output signal 51. The angular encoder 6 is connected via for example antibacklash gears (not particularly shown) to the drive mechanism of the transport mechanism 1. The gearing is such that a set number of pulses essentially equally spaced in time (for example 120 pulses) occur between the time the leading edge of a transport bar (FIG. 2) passes a fixed position on the transport frame (for example a point coincident with the center of an optical head), and the time that the leading edge of the next bar 8 passes that point. The gearing is designed so that when a sync pulse 52a occurs, the relative position of the transport bar 8 nearest any fixed point of the transport frame is constant. Thus, the computer 4 is able to determine at any time the relative position of the transport bar 8 being viewed by each optical head 14 by counting cycles of the first encoder output signal 51 following the occurrence of a sync pulse 52a. The pulse 52a (FIG. 12) appearing on the one line 52 whenever the encoder shaft reaches a given position, serves to synchronize the computer and the transport. Thereafter, in each instance, one hundred twenty pulses per capsule holder bar (cycle) will be fed to the computer via the other encoder line 51. The computer will keep tract of the number of counts since the beginning of each cycle and use said counts since the beginning of a cycle as part of the means of establishing the physical position of capsules relative to the sensor heads.

A program in the computer keeps a bar position counter in the computer core memory. This counter is used by programs to instruct the A/D interface (FIG. 11) as to which signals are to be converted and stored at any time. For each capsule column or flow channel, the four color recognition signals are, in the example of embodiment here depicted, sampled: (1) seven times while one-half of a capsule is in the detector's field of view; and (2) seven times while the other half of the capsule is in the field of view. (Sampling could also occur several times while the blank position of the holder bar 8 is in the field of view if same is (white and) used as a reference). The signals from the two defect recognition sensors for each column or capsule flow channel may be sampled say seventy five times while a capsule is in the detector's field of view.

As illustrated in FIG. 5, the capsule channels and thereby the (optical sensor heads) may be divided into four groups of four, labelled A through D. In each group, the distance (along the direction of motion) between optical sensor heads is preferably a whole number multiple of the front to back width of the holder bars 8. Typically, this holder bar dimension would be one inch. If, by way of example, with the holder bars being one inch wide, and the values for J, K, L, M, S, T and U in FIG. 5 being as given in following table:

| J | 1.5 |
| K | 3.0 |
| L | 0.75 |
| M | 4.25 |
| S | 8.50 |
| T | 12.75 |
| U | 0.75 | then, consequently, with one hundred twenty counts per cycle, corresponding signal samples for each successive group will be taken thirty counts after the signal samples for the preceeding group.

Figure 6:
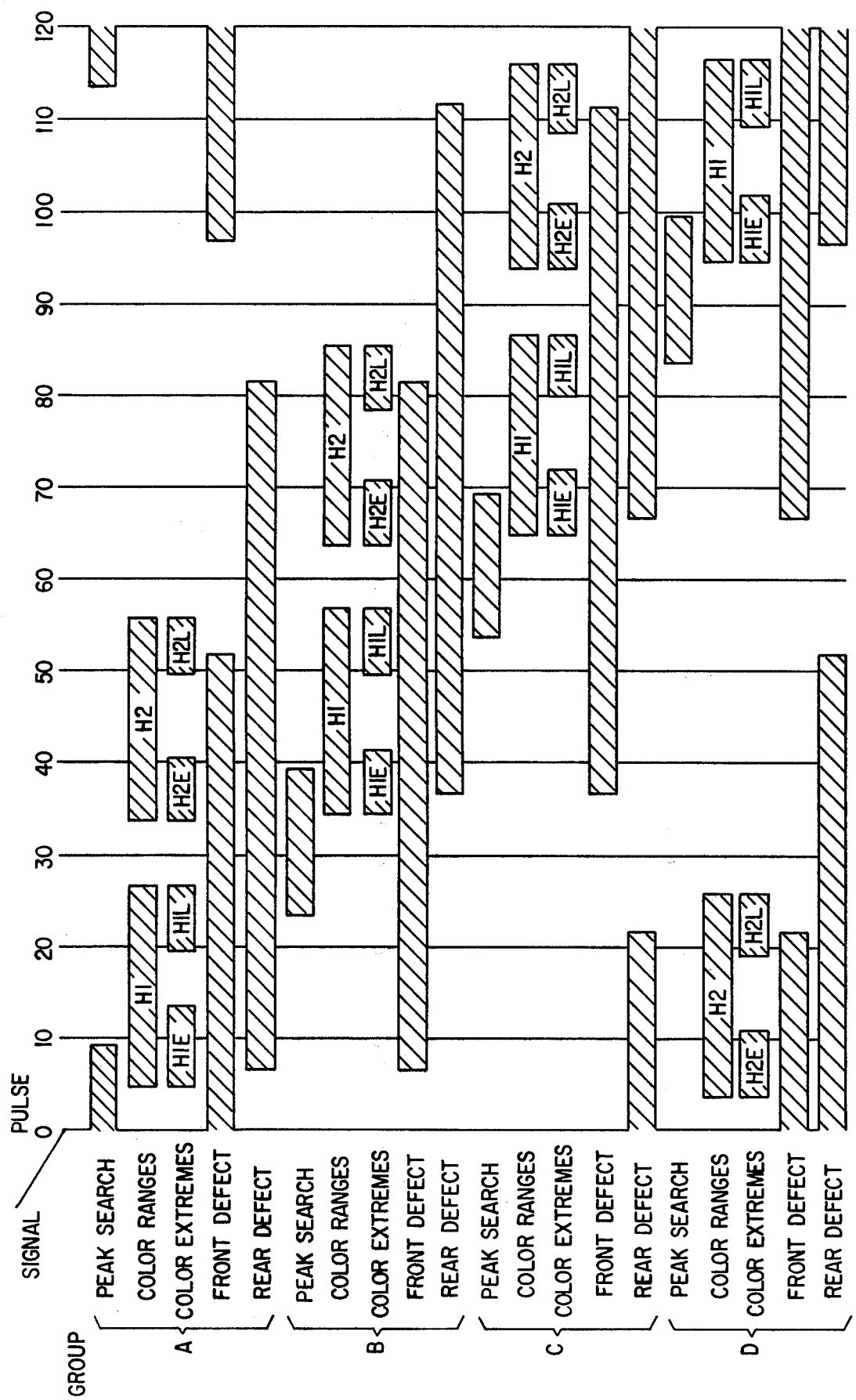
FIG. 6 is a bar graph illustrating in respect to pulse representations of relative capsule position during transport the specular peak, color and defect searches performed in accordance with the invention.

FIG. 6 illustrates the signals which are converted during each interval. As shown herein, H1 and H2 indicate the ranges in which the sensors may be viewing the first capsule half and the second capsule half, respectively. The positions for color sampling are determined by detection of the specular peak (FIG. 13) of the signature received from one detector of the color determination optical system viewing the capsule. FIG. 6 shows the positions sampled in searching for the peaks of the signatures from capsules. H1E and H1L indicate the early and late extremes within the H1 color range at which data for one capsule half may be obtained. Similarly, H2E and H2L are associated with the extremes of the color range of the other capsule half. Actual times of sampling of signals from one capsule half comprise, as indicated above, seven consecutive positions within the sampling range for any capsule, but may differ from channel to channel in a group and from capsule to capsule in a channel depending on when the searched-for peak is found. Thus, H1E and H2E represent color sampling times for the first and second halves, respectively, for a capsule with a peak located at the beginning of the peak search range. H1L and H2L similarly represent sampling times for a capsule whose peak is found at the end of the peak search range.

FIG. 6 also illustrates the sampling times for defects of the front and rear halves of the capsules, for each group of sensor heads.

After all data for one set of four capsules of a group have been accumulated in the computer, these data will be analyzed while the data for a second pair of four capsules (of another group) are being accumulated.

Since noise (e.g. printing on the capsule) will cause significant deviations of the color signals, averaging is advisable to minimize the noise effect. Also, since drift may cause changes in the spectral characteristics of the light source and/or in the photodetector gain, normalization of the color recognition signals may also be advisable. Software programs within the computer perform these tasks. For each color recognition signal, a program essentially provides the following. It averages the seven samples from the first half and the other half of the capsule, respectively. The average calculated for the first half may, if deemed needed, then be divided by a reference value; likewise, the average calculated for the second half of the capsule may be divided by a reference. These two (normalized) average values are then ready for use in a color recognition algorithm. The color recognition and defect determination algorithms are pursued hereinafter.

Figure 13:
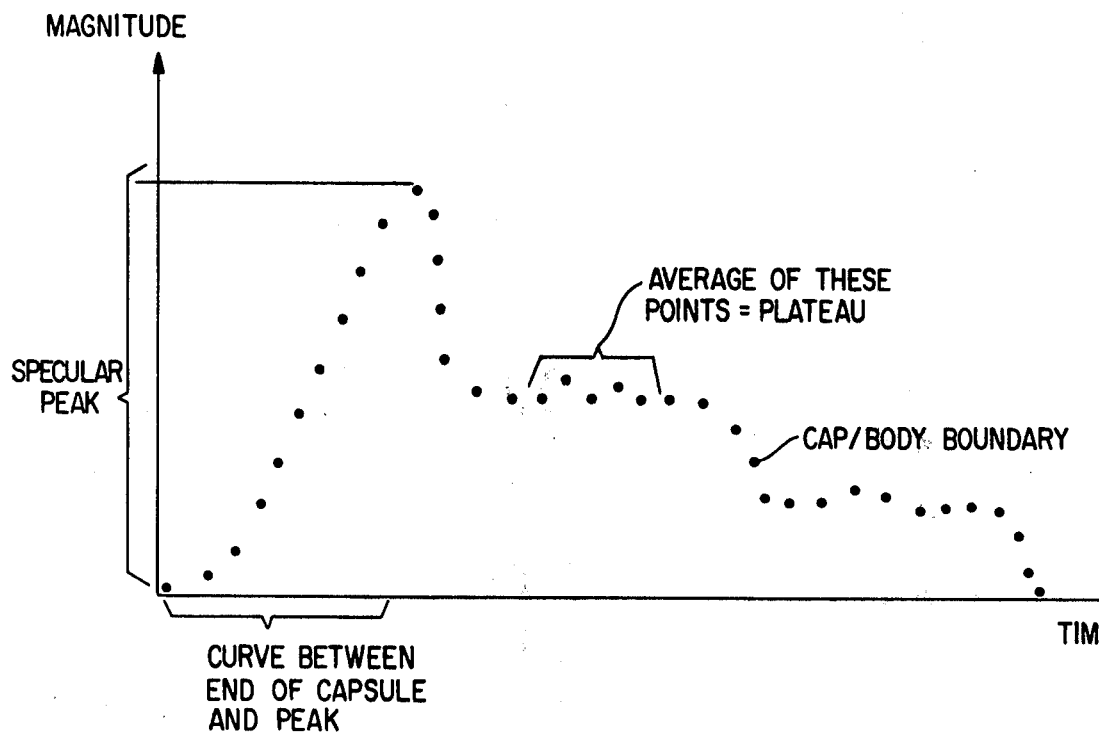
FIG. 13 is a graphical illustration relative to time of a capsule signature signal output from the electro-optics system.

FIG. 13 depicts a typical time history of a portion of an output from one optical channel of the electro-optical subsystem 2. The essentially non-zero portions of this output are caused by the capsule, generally referred to herein as a capsule signature. The computer 4 (as stated) is programmed to read at certain times (relative to the encoder signals 51, 52) certain outputs from detectors associated with an optical head 14 so as to capture essential parts of the capsule signatures. By extraction from the signature of one signal used for color detection of the time of occurrence of at least a certain capsule signature feature (i.e. the specular peak) the computer (program) determines when to read other detector outputs to obtain data concerning the capsule (see e.g. FIG. 6). That is, this peak is used as described hereinbefore as a base computation point by which the computer determines when, for example, the capsule flat portion is coming up. From the data read concerning a given capsule, the computer constructs cap and body color vectors and determines whether the "shape" is acceptable. It also computes from the two sensor signals used for defect detection the values of other significant signature features. FIG. 13 outlines at least some of these features. The peak illustrated in FIG. 13 is the reflectance caused by the capsule's curved end where the angle of incidence is equal to the angle of reflection. Distinguishing signature features include, for example, (1) The number of slope reversals occurring in the waveform leading to the peak.
(2) The plateau value average height of points in a "flat" region of the signature.
(3) Those instances in the waveform leading to the peak where differences from sample point to sample point are greater than a pre-established (threshold) multiple of the plateau value.

(4) The number of encoder pulses 51 from the peak to the midway point (capsule cap/body boundary) between the two flat portions of the total capsule signal which correspond to the two flat viewed portions of the capsule.

(5) The height of the specular peak.

(6) The peak location with respect to the position counter kept in memory.

(7) The number of clock pulses between the peak of the signature from the front view defect sensor and the peak of the rear view defect sensor. These color and signature feature values (or functions of these features) are then compared to acceptable ranges (e.g. previously determined from good capsules). When all the computed values lie in acceptable ranges, the capsule is considered good. When any value lies outside an acceptable range the capsule is considered bad. The computer determines when each bad capsule is under the rejection head, and it causes the rejection head to displace any unacceptable capsule from its holder into a reject channel.

Figure 14:
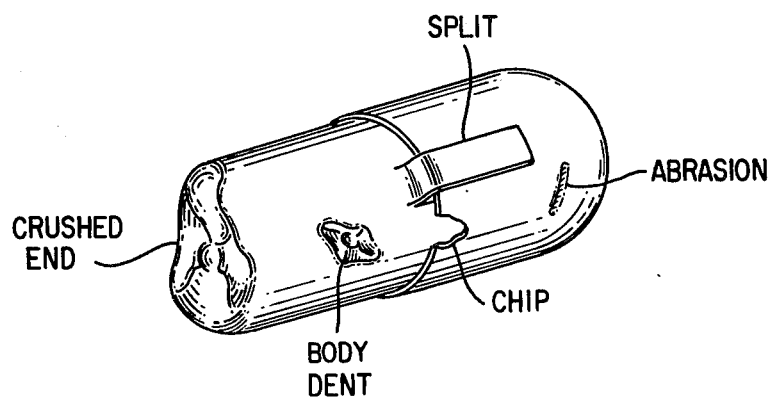
FIG. 14 is a perspective composite illustration of some of the capsule defects which are encountered and detected by an arrangement according to the invention.

FIG. 14 particularly shows in a composite illustration some of the capsule defects which may be encountered and detected by a system according to the invention. These include starred or crushed ends, body dents, splits, chips and abrasions.

In further regard to the rejection of bad material, the color recognition and defect detection algorithms set, for bad material, bits in a reject table. The position in the table is a function of the material's capsule channel and the position of that channel's optical head relative to the rejection head. Tables in the computer memory provide the relative head position information. Another program in the computer "pops" the rejection table at appropriate times and determines when a set of sixteen capsules (actually "set" here is in reference to the sixteen capsule holders constituting a holder bar 80 [FIG. 16]) is about to pass by the air jets of a rejection head (see FIG. 15) relative to the transport. At the correct time, it generates digital signals as determined by the top word of the reject table which activate certain jets so as to reject improper (bad) capsules in the set.

With reference to FIG. 15, the reject head comprises a multiple air jet arrangement consisting of one air jet 71 per capsule channel. Air flow from a common intake 72 to each jet is controlled, for example, by a fast-action solenoid valve 73, which may be a modified commercially available solenoid, such as a Skinner B2DA917 valve. Although not particularly shown in FIG. 15, the valves in turn are individually controlled by the signals (outputs from the UIM board) from the computer.

With reference to FIG. 16, the jets are used to blow capsules from the capsule holders 81 in the transport bar 80 to grooves 82 between the capsule holders. With reference to FIG. 15 shields 74 are provided on the reject head to prevent a particular air jet from affecting more than one capsule on a transport bar 80.

Figure 17:
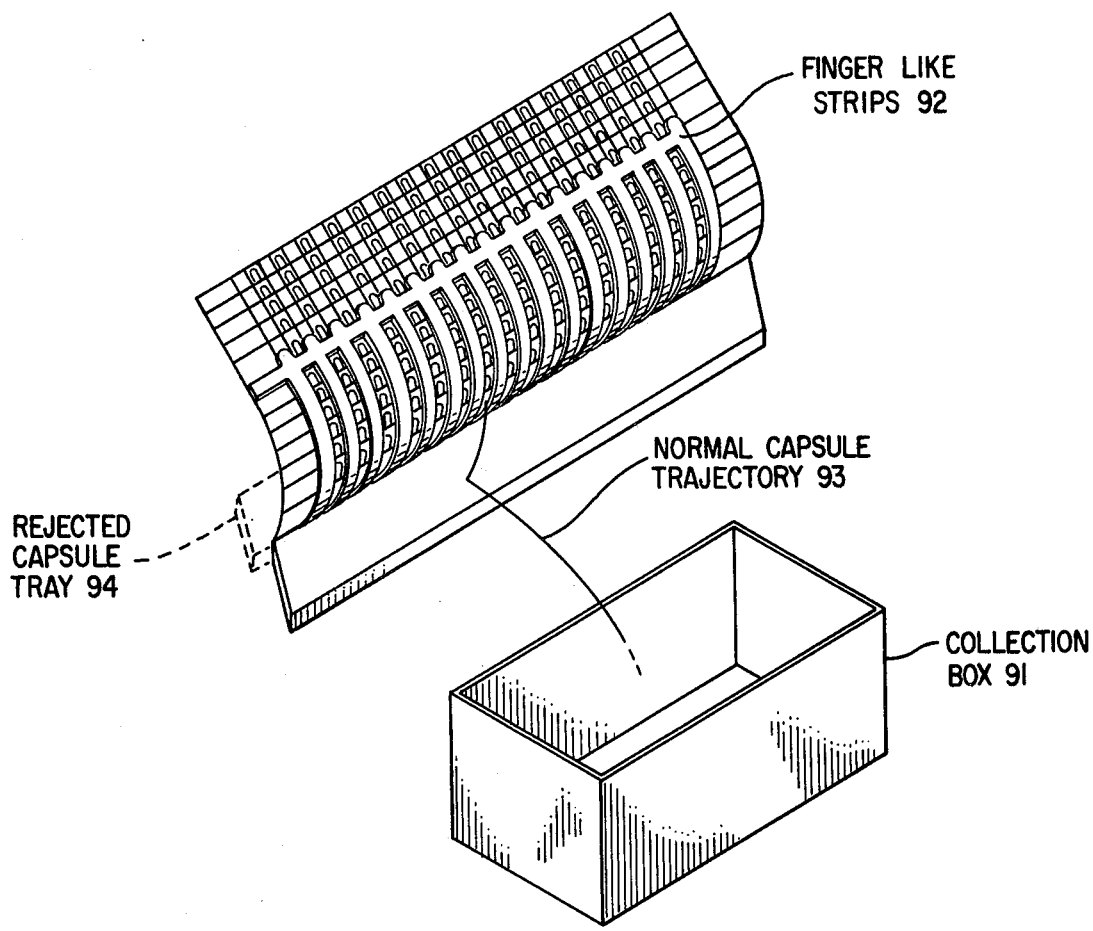
FIG. 17 is a perspective view of the end of the transport mechanism and illustrating the means for completing the separation of the rejected capsules from acceptable capsules.

With reference to FIG. 17, capsules not acted upon by the air jets are allowed under the action of gravity to fall into a collection container 91 at the end of the transport 1, for example, in a normal capsule trajectory 93. Rejected capsules lying in transport bar grooves 82 are guided underneath the transport by finger-like metallic strips 92. From there the rejected capsules are guided into a rejected capsule tray 94.

The computer 4 keeps a count of all good capsules passed under the optical heads. It displays on the display panel thereof the number (truncated e.g. to the nearest thousand) and after completion of an entire inspection cycle prints out the exact count.

Figure 18:
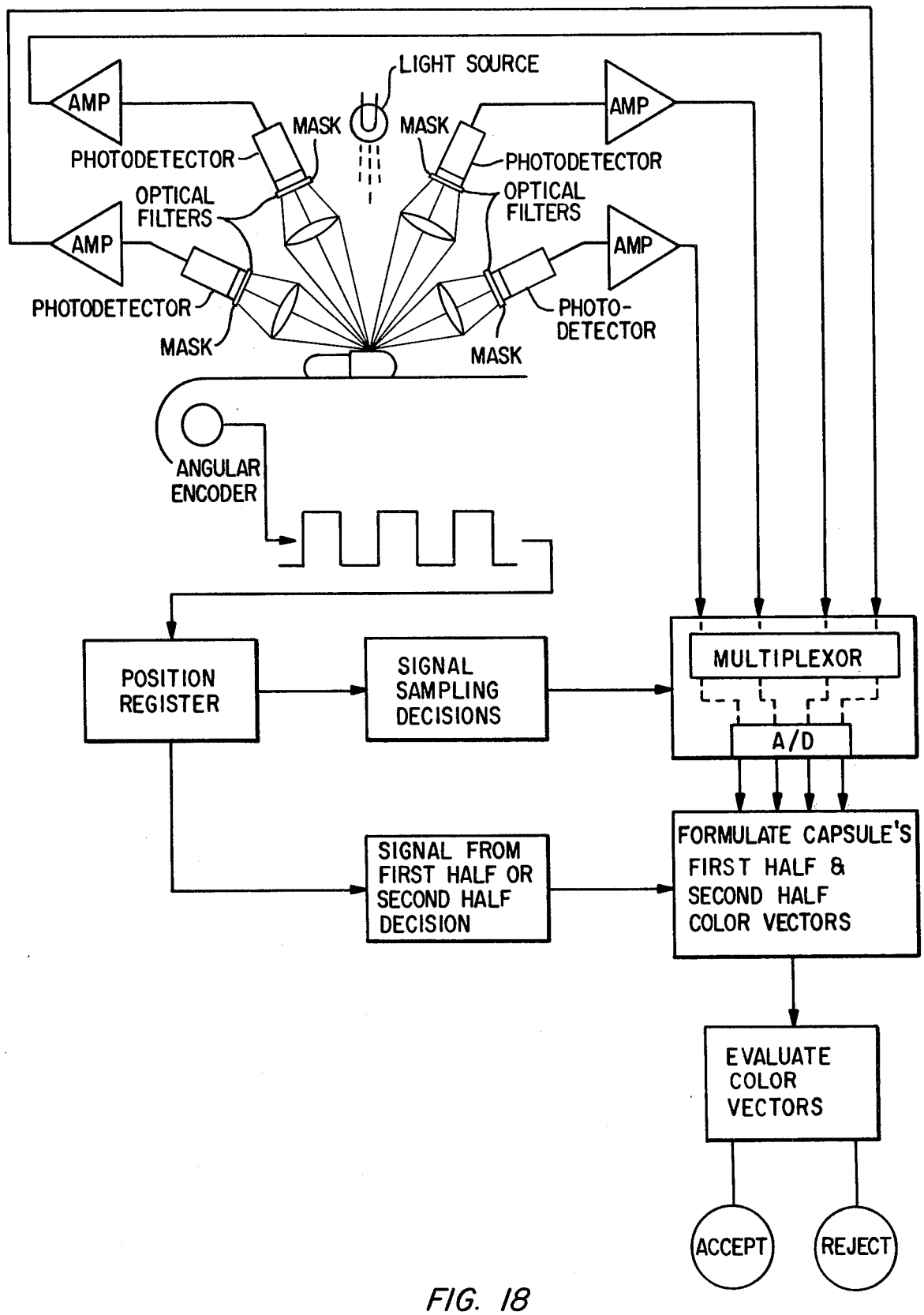
FIG. 18 is a schematic block diagram illustrating broadly the operation of color recognition in accordance with the invention.
Figure 19:
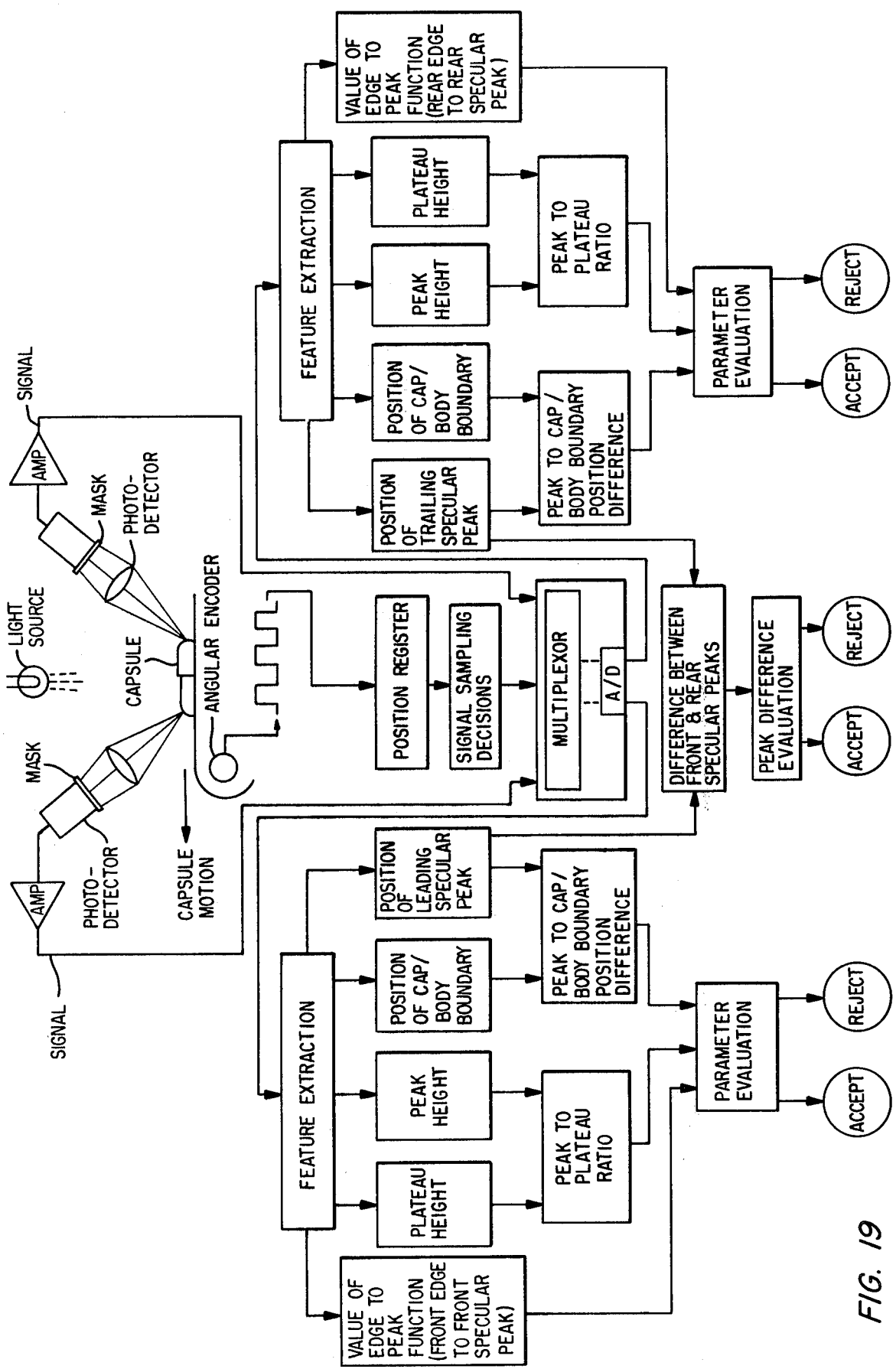
FIG. 19 is a schematic block diagram illustrating broadly the operation of defect detection in accordance with the invention.
Figure 20:
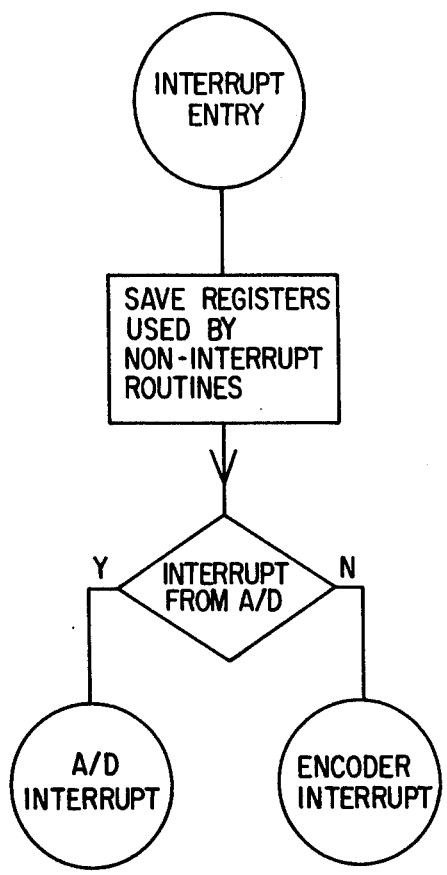
FIG. 20 is a general flow diagram relating to the interrupt operations of the computer of FIG. 1.
Figure 23:
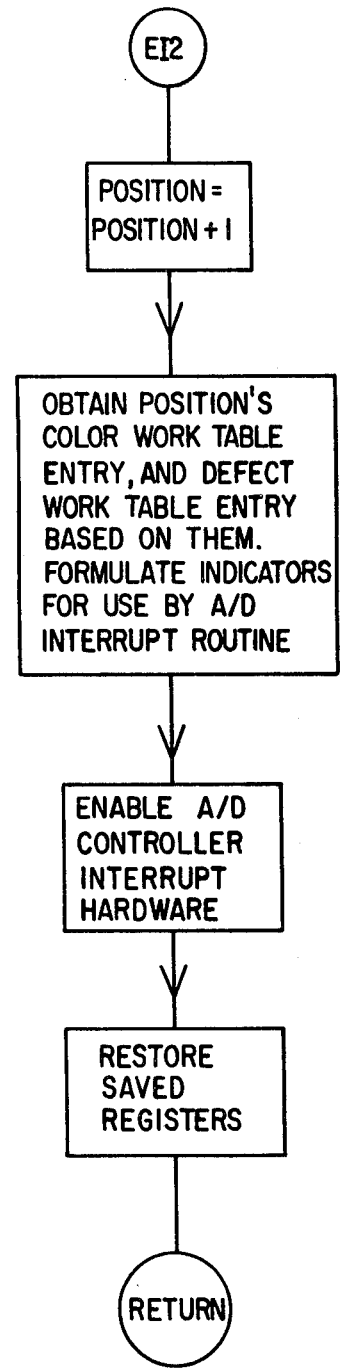
FIGS. 21-23 are flow diagrams detailing the encoder interrupt routine of FIG. 20.
Figure 21:
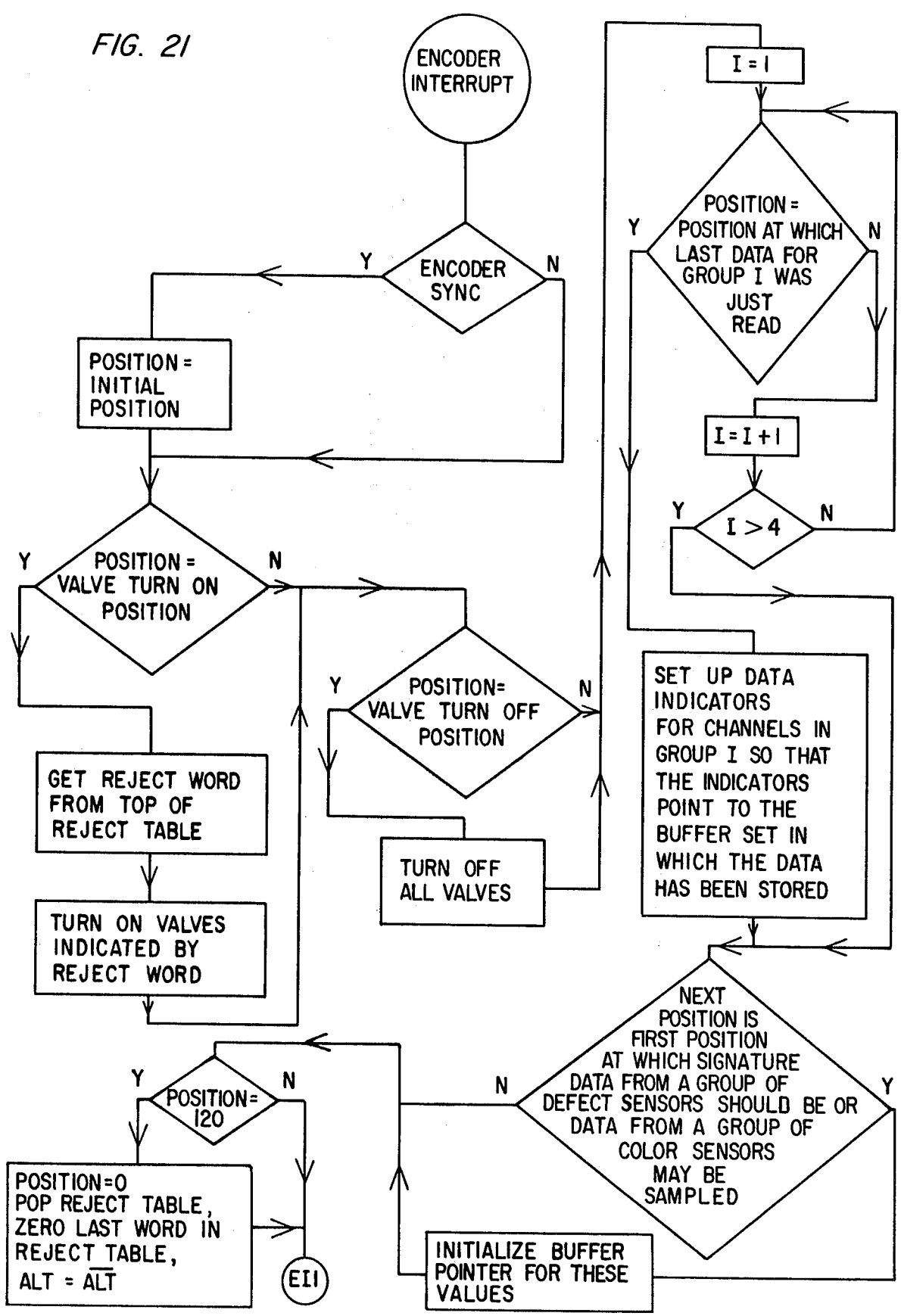
Figure 22:
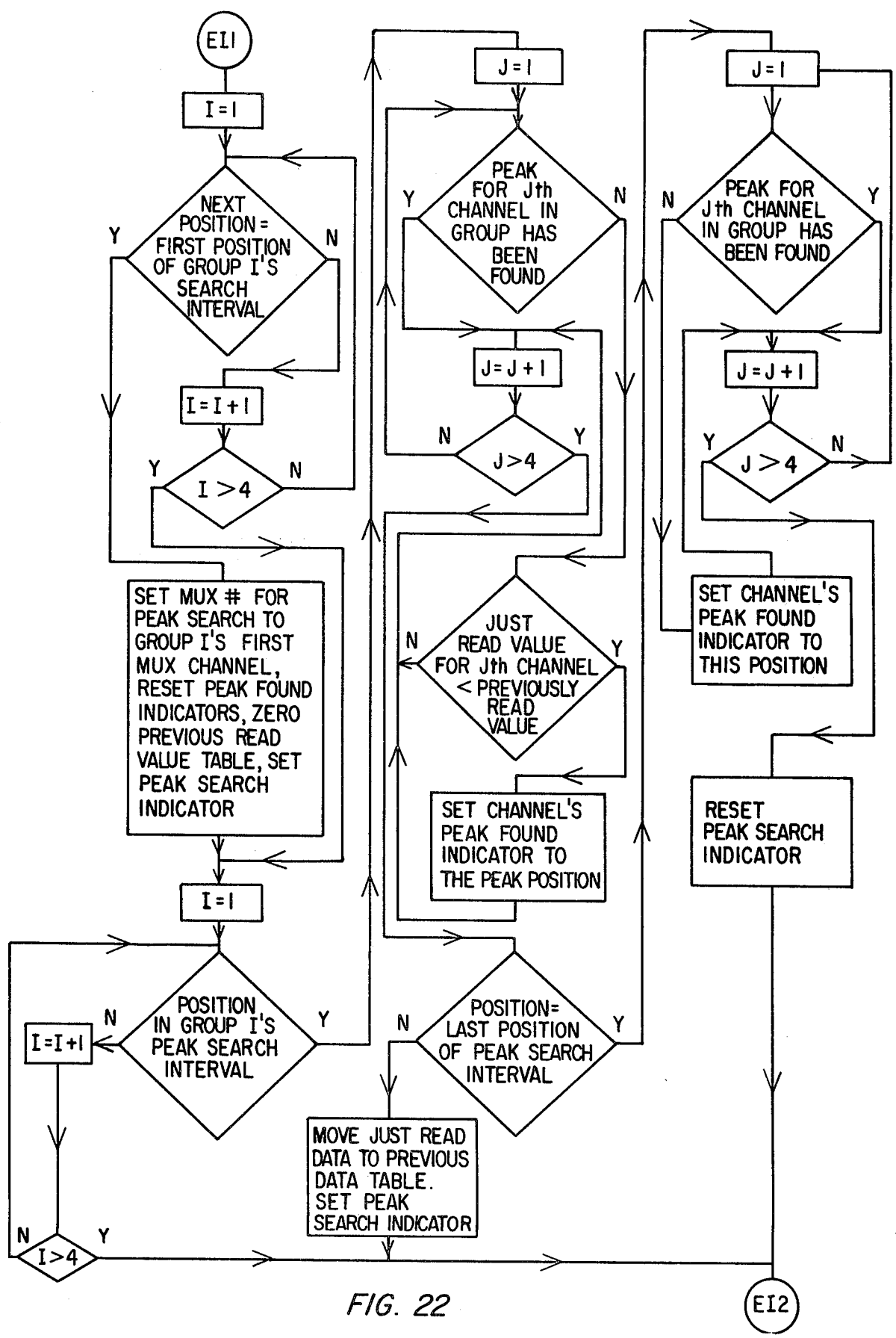
Figure 24:
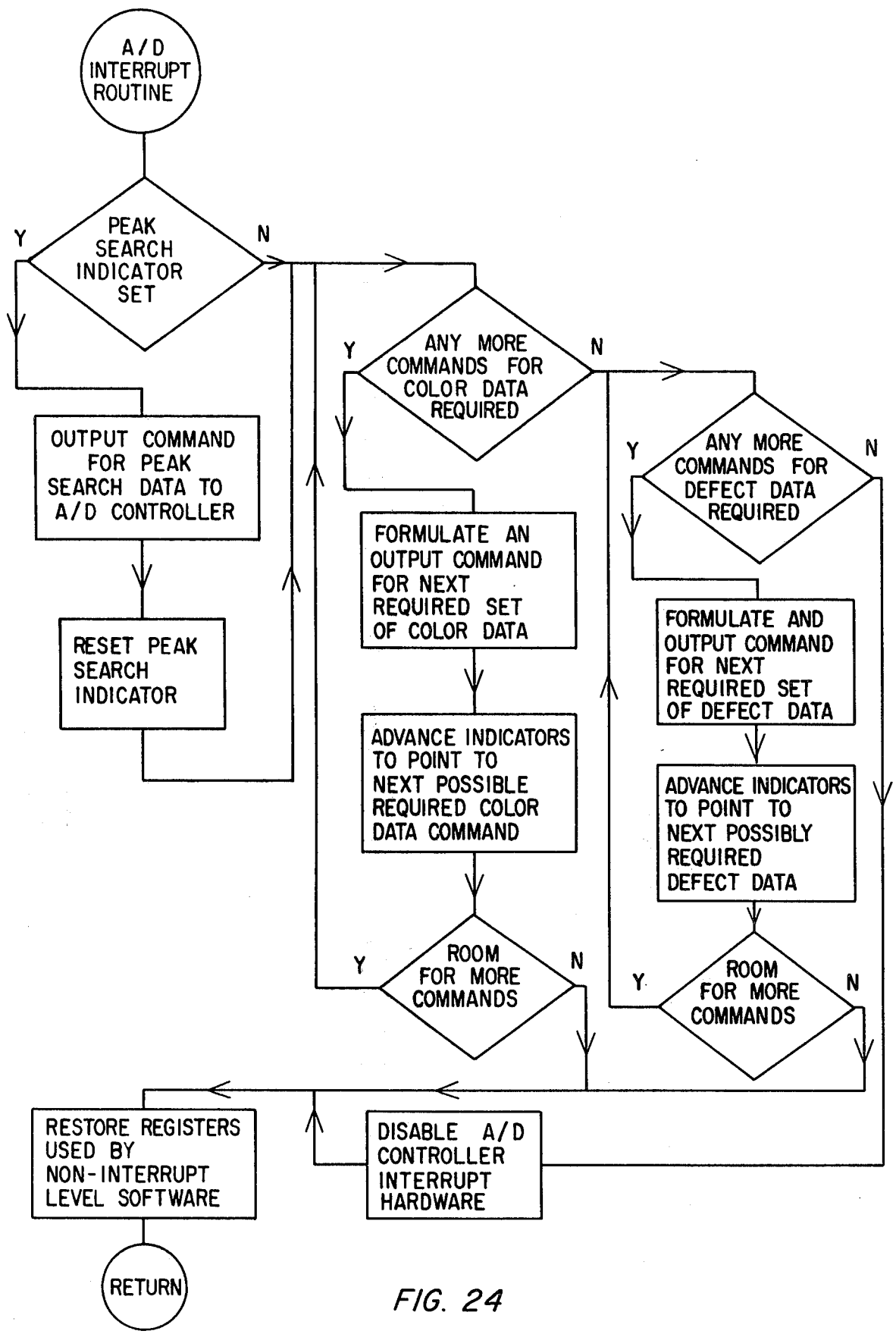
FIG. 24 is a flow diagram detailing the A/D interrupt routine of FIG. 20.
Figure 25:
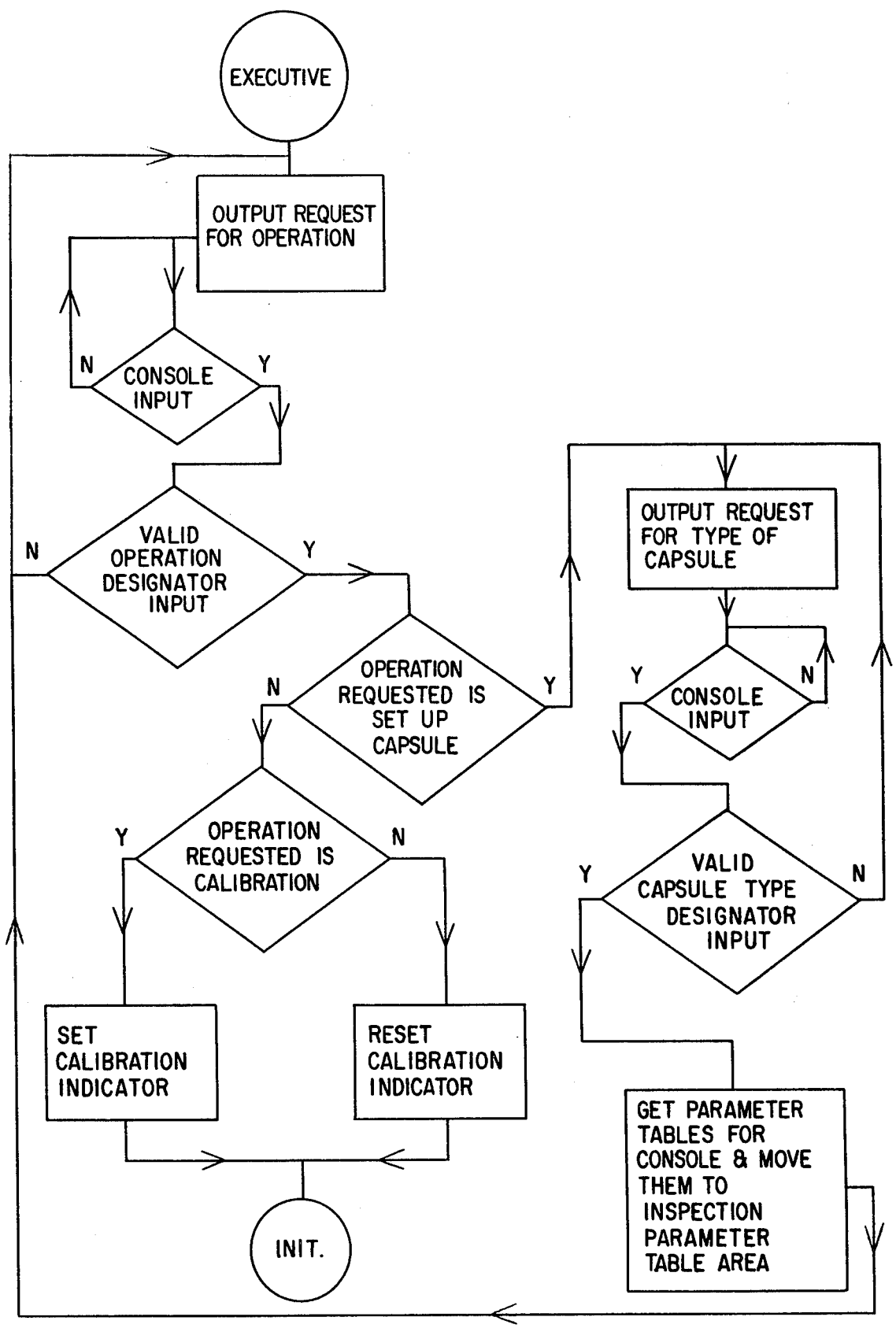
Figure 26:
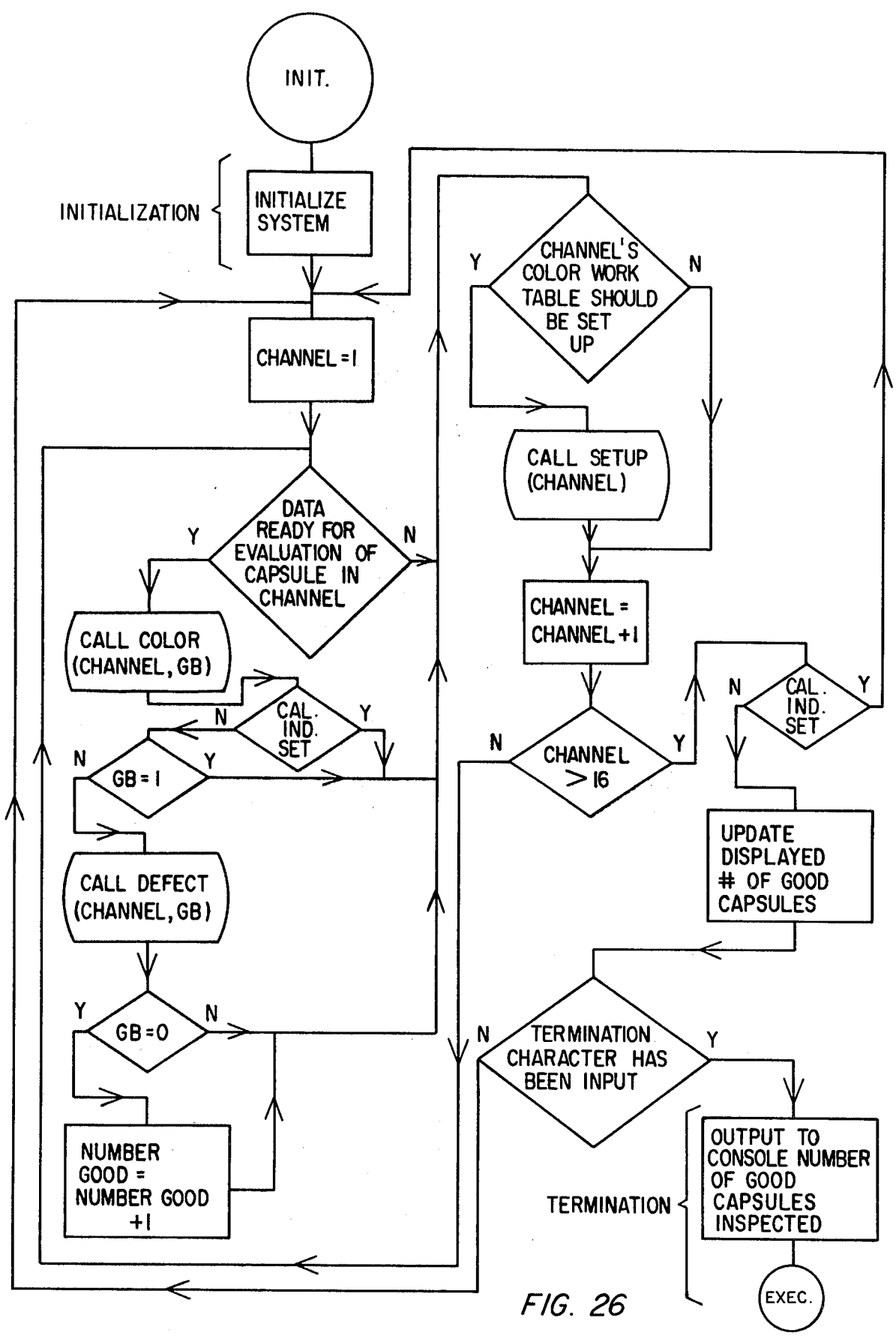
Figure 27:
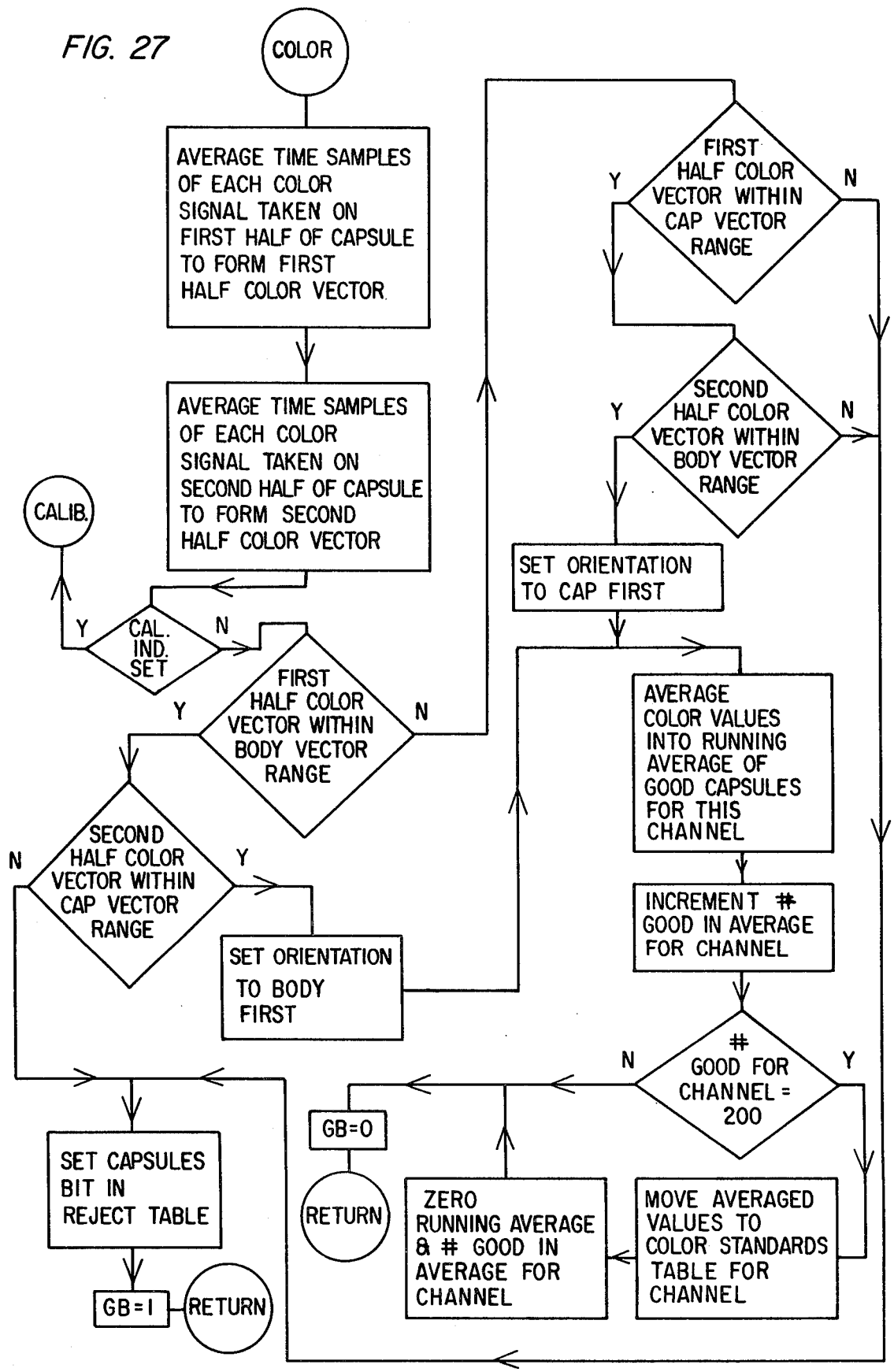

More specific reference will now be made to the software aspects of the system. FIGS. 18 and 19 which are conceptual diagrams of system operation have been provided to assist in the understanding thereof, along with the flow diagrams of FIGS. 20–30. FIG. 18 depicts schematically the relationship between the system hardward and software for the color recognition aspects of the invention. Similarly, FIG. 19 schematically shows the hardware/software relationship for the defect detection aspects of the invention. It should be noted (in regard to FIGS. 18 and 19) that only one signal path exists from the A/D, and the multiplexer address determines which signal is represented by the A/D output.

The computer software in the preferred embodiment may be considered to operate at two levels: the interrupt level and the non-interrupt level. The interrupt level software is responsible for:

1. Commanding the analog-to-digital conversion subsystem controller (A/D controller) in such a manner that the necessary data for evaluating capsules is obtained by the computer (from the optical subsystem via the A/D subsystem).
2. Controlling the reject system's reject valves so that "bad" capsules (which are determined to be bad by the non-interrupt software) are rejected.
3. Controlling indicators which signal the non-interrupt software as to when complete data on capsules has been obtained and as to where that data is located in the computer's memory. The non-interrupt level software is responsible for:
1. Evaluating the capsule data and determining which capsules are "good" and which are "bad".
2. Setting for each bad capsule a bit in a reject table (used by the interrupt level software in its reject valve control function).
3. Performing at the non-interrupt level, as dictated by indicators set up by the interrupt level software, functions necessary for allowing the interrupt level software to perform its first function listed above.
4. Displaying on the computer's display panel the number of good capsules (truncated to ignore the hundreds through units places).
5. Setting up for inspection of the particular type of capsule requested by an operator.
6. Performing calibrations of the system.

Two separate sets of buffers (areas of computer memory) are used for capsule data. (Particular data for a capsule from a specific physical channel is always located in a fixed location relative to the start of either buffer set.) The use of two sets of buffers allows data stored in the buffer concerning a capsule in a particular channel to be evaluated while data concerning the next capsule in that channel is input into the other buffer.

The interrupt software consists of three routines. These are:

1. The Interrupt Entry Routine
2. The Encoder Interrupt Routine
3. The A/D Interrupt Routine In reference to FIG. 20, the computer enters the interrupt software when its hardware detects an interrupt condition. Interrupt conditions occur when:

1. the encoder's higher frequency output line is raised;

2. the A/D controller's interrupt hardware is enabled and the controller's command registers are empty.

When such a condition is detected the computer stops running the non-interrupt level routine (in such a manner that it can be restarted, after the running of the appropriate interrupt routines, at the point it was stopped at) and starts the Interrupt Entry Routine. This routine determines which interrupt condition exists and based on this transfers to the Encoder or A/D interrupt routine.

In reference to FIGS. 21-24 the Encoder Interrupt Routine first reads the value of the encoder's sync line. It maintains a position counter (giving a relative capsule holder position) which it initializes if the sync line is high. It next checks the position counter to determine which if any of a set of conditions are true. For each true condition it takes a specific action. The conditions and the actions are:

| Condition | Action |
| --- | --- |
| 1. The position is the reject valve turn on position. | The valve turn-on word at the top of the reject table is fetched and the valves indicated by the word are turned-on. |
| 2. The position is the reject valve turn-off position. | All valves are turned-off. |
| 3. The position is a position of which the last data needed for evaluation of a group of capsules has just been received. | An appropriate value pointing to the buffer sets in which the information is stored is inserted into data in indicators for each channel within the group. |
| 4. The position is the maximum position (120). | The position indicator is zeroed, the reject table "popped" and its new last word zeroed, and a buffer alternate indicator set to point to the alternate buffer set (the set other than the one it was just pointing to). |
| 5. The position is a position which is just prior to the first position of which a group of sensors may see peak signals (from the capsules they are viewing). | Tables and indicators will be set up to search for the relative maximums (peaks) of the signals from these sensors (this is the beginning of a procedure which for color evaluation ensures that the proper data is obtained despite the fact that there is some small uncertainty as to the relative position of a capsule within a capsule holder). |
| 6. The position is a position which is just prior to the first position at which signature data from a group of defect sensors should be sampled or data from a group of color sensors may be sampled. | A pointer to the memory locations in which this data is to be stored is initialized. |

Upon completing the above checks and any actions based on those checks the routine determines if the position is within the peak search range of any group of sensors. If it is, the routine determines which, if any, of these sensors' signals have previously gone through relative maximum in the search interval. For each of those signals which have not, the routine checks its last two converted values to determine if it has just gone through a relative maximum. When it determines that a signal has just gone through a relative maximum the routine sets a peak found indicator so as to indicate the position of the peak. This indicator will cause the non-interrupt software to set up a color work table so as to guarantee that the values of signals needed for evaluation of the color of the capsule viewed by the sensor whose signal has just peaked will be obtained at the proper times. Upon completing any necessary checks for peaks, the routine checks if the position is at the end of a peak search interval. If it is, the routine acts as if it has just found a peak for any of the signals whose peaks it is searching for but has not previously found. It also resets certain indicators so the signals whose peaks it is searching for will not be immediately sampled again by the A/D system.

Upon completing the peak search procedures the routine increments the position counter and fetchs the new position's entries from the color work table and a defect work table. Based on these fetched entries it sets up certain words and registers for use of A/D interrupt routine. The setting up of these words and registers together with the setting up of indicators for obtaining peak search data determine the sensor signals which will be converted and stored in the computer by the A/D subsystem between this and the next running of the Encoder Interrupt Routine.

Finally, the Interrupt Entry Routine enables the A/D controller interrupt hardward so it will interrupt the computer when its command registors are empty and then commands the computer to restart the interrupted program.

The A/D Interrupt Routine formulates commands to the A/D controller based upon information developed by the Encoder Interrupt Routine. Each command takes the form of a three-word output from the computer to the controller. Those words contain:
1. a computer memory address (ADR);
2. an A/D subsystem multiplexer address (MUX) which is directly related to a sensor signal;
3. a number (n) of conversions and a function. As described hereinbefore, the controller operates upon the commands by: (1) causing the A/D converter to convert successively the signals connected to the multiplexer inputs starting with the multiplexer input at address MUX and ending with the multiplexer input whose address is MUX + n−1; and (2) as these conversions are completed, directly storing the results into successive computer memory locations starting with location ADR. (The stored result will, depending on the function specified in the command, be either the converted value or the sum of the converted value and the previously stored value.)

After completing the outputs of a command the A/D Interrupt Routine checks if the A/D controller is able to accept another command. When the controller cannot, the routine commands the computer to return to the interrupted program. When another command can be accepted the routine checks if all commands for the A/D controller have been output to it. When they have not the routine formulates and outputs the next command. When they have, the routine disables the A/D controller's interrupt hardware (as the A/D Interrupt Routine will not be called again until after the next running of the Encoder Interrupt Routine) and commands the computer to return to the interrupted program.

Referring to FIGS. 25-30, the non-interrupt level software consists of an executive, two evaluation subroutines and a color work table set up subroutine. The evaluation subroutines are a color evaluation routine and a defect evaluation routine. The executive consists of a preinitialization section, an initialization section, a master loop and a termination section.

In the preinitialization section, the executive requests the type of operation required. This request may be for a capsule type setup, calibration, or inspection. The request is made through the output of a message to the console typer. The program then waits for an input from the console. When it receives one it determines what operation is requested. When a capsule type (e.g. Librium ® 10 mg, Librax ® etc.) setup is requested the executive outputs a message to the console asking which capsule type the system should be set up for. When it then receives console input it determines from the input which capsule type it is to set up for and copies the capsule type's parameter tables from the portion of memory they are stored in into the inspection parameter tables area of memory. The program then transfers to the beginning of the preinitialization section. When a calibration operation is requested, the program sets a calibration indicator and enters the program's initialization section. The effect of this indicator will be described hereinafter.

When the computer is requested from the keyboard to begin an inspection (an inspection cycle is from the time the operator requests the computer to commence inspecting to the time the computer is instructed to cease inspecting), it resets the calibration indicator, enters the executive's initialization section, and then on completion of the initialization it enters the master loop. For each channel the master loop periodically checks the channel's data in indicator. When this indicator indicates that data input for a capsule in the channel is complete the loop calls the color evaluation and defect evaluation subroutines. It by-passes the defect evaluation subroutine if the return from the color evaluation subroutine indicates that the capsule does not have the proper colors. If the returns from these subroutines indicate the capsule has the proper colors and no detectable defects, the master loop increments a good capsule counter. After making calls to the evaluation subroutines the master loop zeros the channel's data-in indicator. Upon completing the operations concerned with checking the readiness for and if necessary performing the evaluation of a channel's capsule data, the master loop checks if the channel's color call indicator indicates that its color calls should be set up in the color call work table. If the indicator calls for such a setup the master loop calls the color work table set up subroutine. The master loop also periodically updates the displayed truncated good capsule count and periodically checks if a termination character has been input from the keyboard. If a termination character was received the executive enters the termination section in which it outputs (to the printer) the number of good capsules inspected during the inspection cycle and then transfers to the start of its preinitialization portion.

The color evaluation subroutine (FIG. 27) is entered with the capsule channel number as a parameter. The routine for each capsule half extracts the sum of the seven samples of each color determination signal read when the sensors were viewing that half. The summations have been performed and the sums stored by the A/D controller. Each of these signals is averaged by dividing by seven and the averaged values form color vectors, one for each capsule half. The routine also computes valid ranges for the capsule's body and cap color vectors (from standard vectors and allowable deviations stored in memory). The subroutine then compares the first and second-half color vectors to the body and cap valid ranges. If the first-half and second-half color vectors lie respectively within the body-valid range and cap-valid range or respectively within the cap-valid range and body-valid range, the capsule is determined to have the proper colors. Otherwise it is determined to have improper colors. If the capsule has the proper colors an orientation indicator (cap-first half or body-first half) is set up for use in the running average calculation performed by this subroutine and for use in the defect evaluation subroutine. The color values are then averaged into a running average for this channel and the number of good capsules in the average is incremented. If the number in the average is then 200 the average is moved to the channel's standard color vectors table (thus serving as a recalibration of the system) and the channel's running average and number of capsules in that average is zeroed. Finally, a bad capsule indicator is reset and the subroutine returns to the master loop. If the subroutine determines that the capsule does not have the correct colors it sets the capsule's reject bit in the reject table, sets the bad capsule indicator and returns to the master loop.

The defect evaluation subroutine (FIG. 28) is entered with the channel number as a parameter. It first finds the location in the data buffers of the two signatures (one from a sensor which views the capsule from the front and the other which views the capsule from the rear). It then calculates, for example, the following parameters of each signal (see FIG. 13 for clarity):

1. a peak to plateau ratio;
2. a value indicating the regularity of the signature in the region between the peak and the nearest end of the capsule, such value equalling the sum of the number of slope reversals and number of times successive point differences exceed a value proportional to the plateau;
3. the position difference between the peak occurrence and the cap-body surface boundary. It also calculates the position difference between the occurrence of the peaks of the two signatures (one derived from the sensor viewing the oncoming capsule and the other derived from the sensor viewing the capsule as it moves away). It should be noted that whereas FIG. 13, for example, depicts only a signature derived from the sensor viewing the oncoming capsule, the other signature (for a good capsule) is similar except the peak signature characteristics are present at the end of rather than the beginning of the signature.

After calculating these parameters the subrouting determines the computer memory location of permissible ranges of the parameters for this capsule's orientation. It then compares the calculated parameters to the permissible ranges, and if all of the parameters lie within the ranges the capsule is deemed good. Otherwise, it is deemed bad. If the capsule is deemed good the subroutine returns to the master loop. If the capsule is deemed bad the subroutine sets the capsule's bit in the reject table, sets a bad capsule indicator, and returns to the master loop.

Referring to FIG. 29, the color work table set up routine is entered with channel number as a parameter. The routine fetches the position at which the channel's peak was detected. From this it determines at what positions color data should be obtained for the capsule being viewed by this channel's sensors. It then alters the color work tables entries for those positions so that color data will be obtained at those positions. It then resets the channel's color work table indicator and returns to the master loop. As noted hereinbefore, the request for a calibration causes the executive to set a calibration indicator and then enter its initialization section. The software operation for a calibration is thus identical to that for an inspection except for the alterations caused by the set calibration indicator. Within the executive (see FIG. 25), the set calibration indicator causes the program to skip calls to the defect subroutine, updates of the display of the number of good capsules, and checks for a termination input from the console. In the color subroutine (see FIG. 27) the set calibration counter causes a transfer to a calibration portion of the subroutine after the generation of the observed capsules color vectors.

Figure 30:
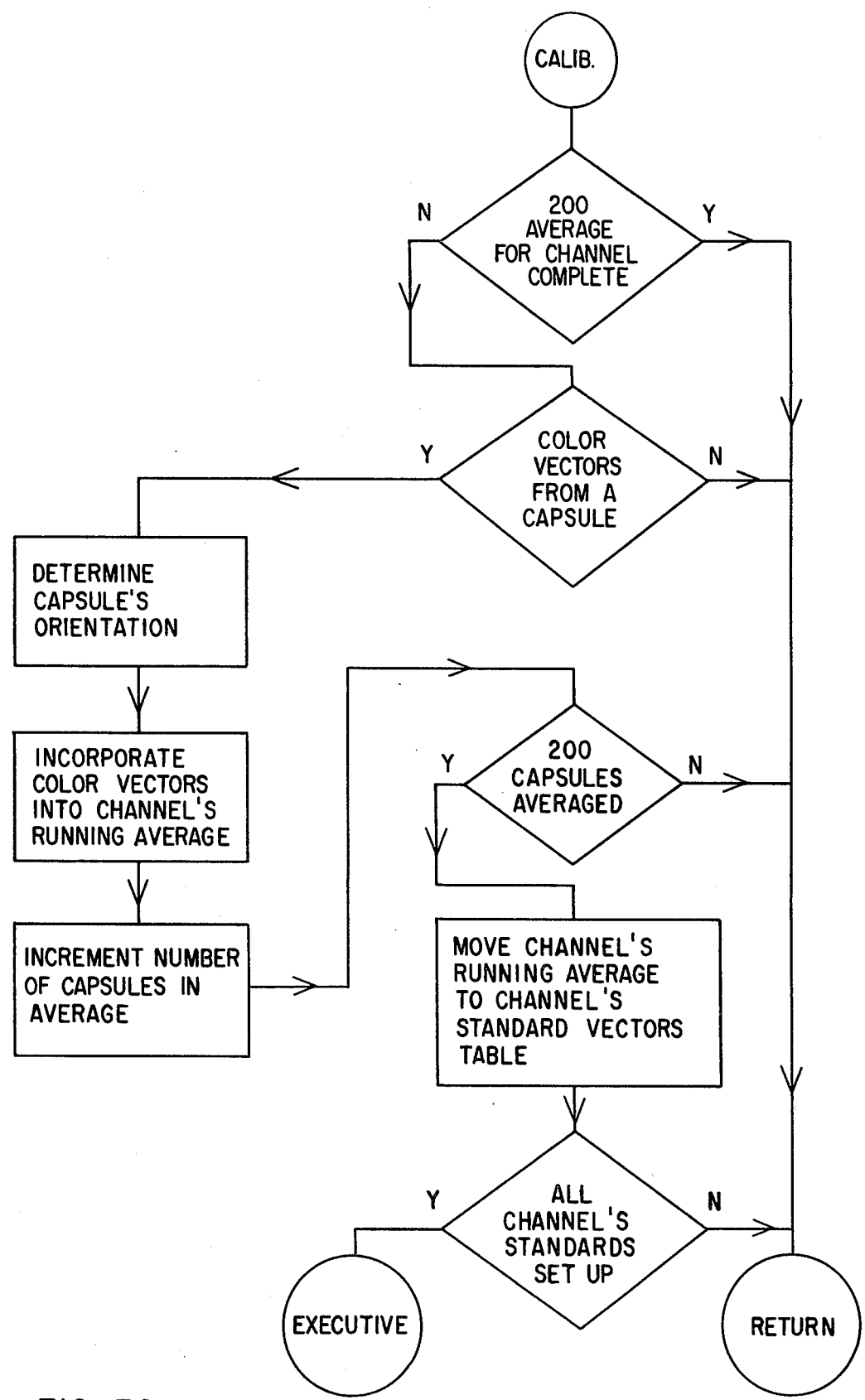

The operation of the calibration portion of the color routine, see FIG. 30, begins with a check of whether 200 capsules have been averaged for the channel. If 200 have not been averaged, the observed color vectors are compared to a threshold to determine if the vectors are from a capsule (or e.g. from an empty capsule holder). If color vectors appear to be from a capsule, the orientation of the capsule is determined from the vectors and the cap and body vectors are averaged into a running average of the channel's color vectors. The number of capsules in the average is incremented and is then checked to see if it is 200. If it is, the running average of the vectors is moved to the channel's standard vectors table in the computer's memory and a check is made to determine if the standard vectors have been set up for all sixteen channels. If they have a transfer is made to the beginning of the executive's preinitialization section. Should in the checks made above, 200 capsules already be averaged, the observed vectors not appear to come from a capsule, 200 capsules are not yet in the average after an averaging operation, or all channel's standards have not been set up, a normal return to the executive's master loop will be made.

Figure 31:
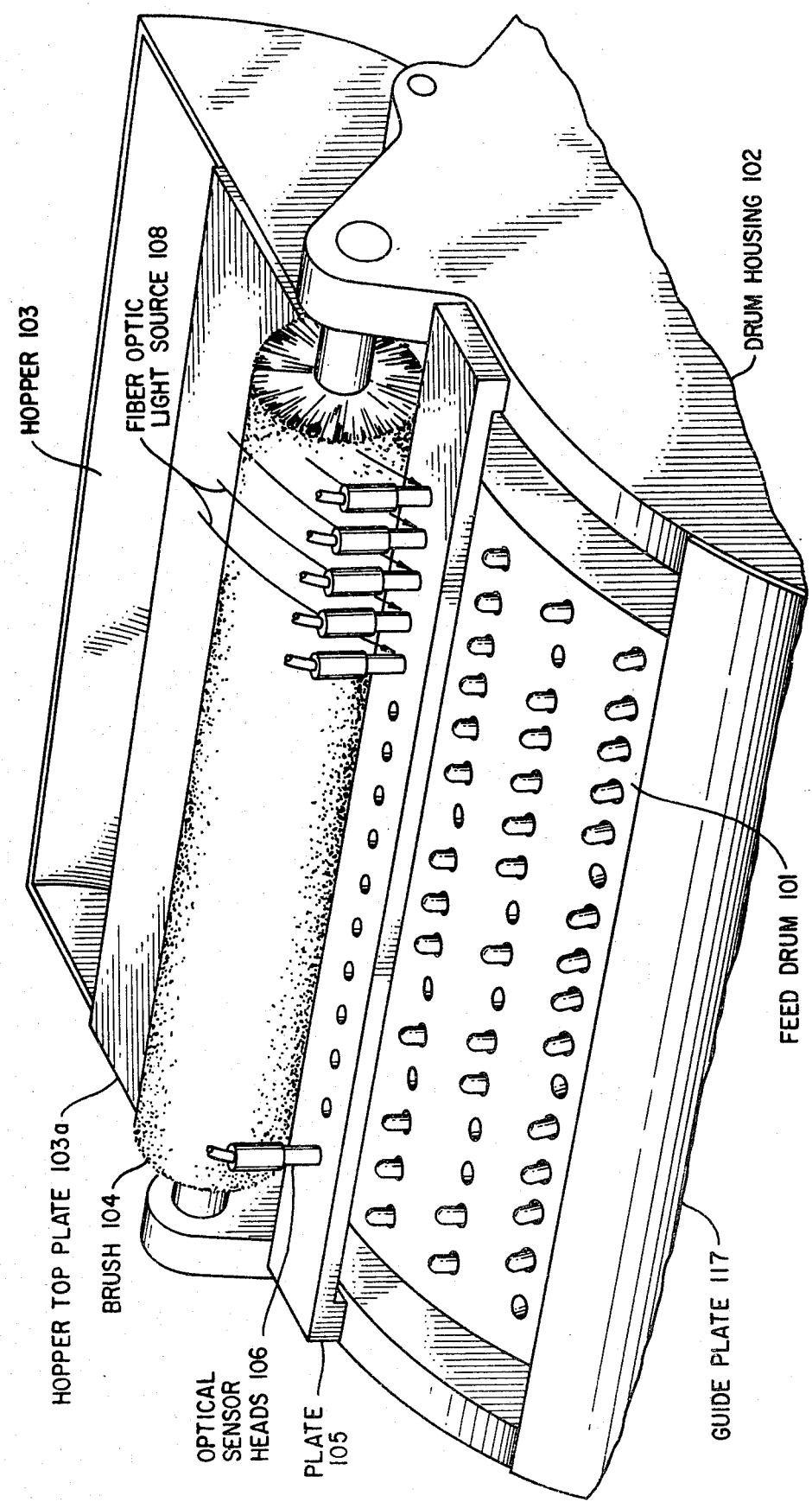
FIG. 31 is a perspective view illustrating a portion of the transport means presenting capsules end-on for inspection.

Referring to FIG. 31, there is illustrated therein an arrangement for enabling a more detailed inspection of the two capsule ends, for purposes of defect detection. This arrangement is intended to operate in connection with a suitable horizontal transport such as is described hereinbefore. Shown in FIG. 31 is a feed drum 101 mounted in a drum housing 102, which drum preceeds and communicates with the horizontal transport, such as is the case, for example, in the capsule printing machine of the R. W. Hartnett Company referred to hereinbefore. The feed drum has associated therewith a hopper 103 having a top plate 103a, in which hopper capsules are placed to be derandomized and picked up by the feed drum 101. Assisting in this regard may be a brush or other suitable arrangement 104 operating in a well known manner such as is depicted in FIG. 31.

Mounted above the feed drum 101, at a position relative thereto in which capsules already are loaded into the drum slots (oriented perpendicular to the drum surface) is a plate 105, for mounting N (# of capsule flow channels) number of optical sensor heads 106, preferably one for each channel. Schematically illustrated in FIG. 31 as a series of arrows are N fiber optic type light sources 108 operatively arranged with the optical sensors 106 to illuminate the capsules as they pass beneath the heads. It should be noted that the optical sensors 106 may employ bifurcated or other fractionalized fiber optic type arrangements and more than one fiber optic light source may be used per channel. By mounting the optical sensor heads above the drum as indicated, a view of the capsules moving perpendicular to their axes of symmetry can be readily obtained. This view particularly provides greater sensitivity to small end defects such as "star ends".

This embodiment of capsule inspection system, thus, contains a transport which, at some point, presents to the optical sensors capsules moving perpendicular to, and at another point, parallel to their axes of symmetry (the horizontal transport portion).

Figure 32:
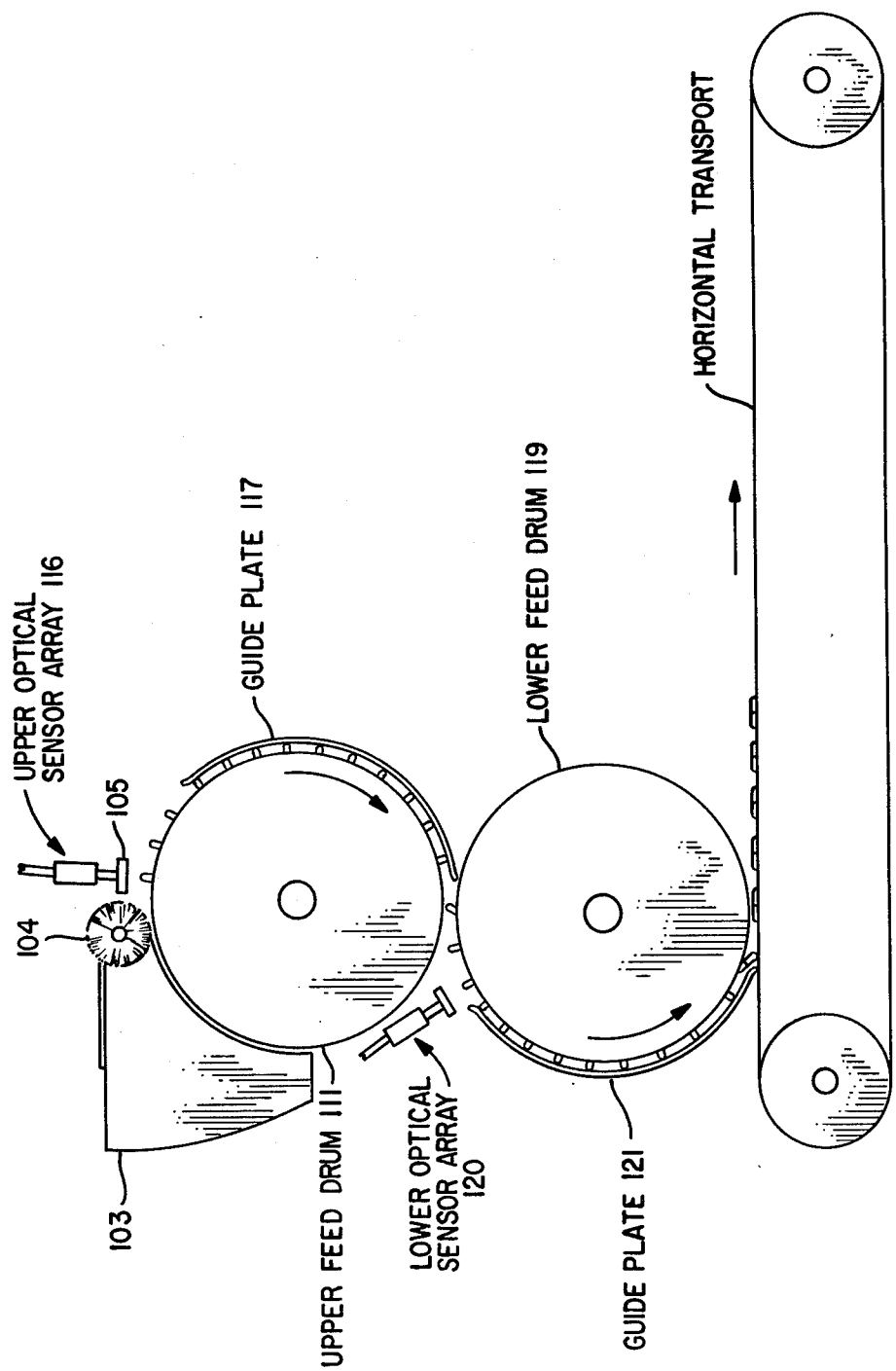
FIG. 32 is a schematic diagram illustrating a portion of a transport arrangement presenting both ends of the capsules for inspection.

The system may be such that a capsule is viewed by sensors on both ends (simultaneously or one end at a time) while moving perpendicular to its axes of symmetry, in addition to being viewed as described above by sensors as it moves parallel to its axis of symmetry. A transport system of this type could be comprised of a second drum (FIG. 32). In the schematic illustration of FIG. 32, the hopper 103 and brush 104 are shown as before, only this time arranged in connection with a first or upper feed drum 111. Drum 111 has associated therewith (via a plate support 105) an array of optical sensor heads 116, not unlike that of FIG. 31. Also, associated with drum 111 is a guide plate 117 for retaining the capsules in their slots as they are rotated around to the underside of the upper feed drum 111.

In the arrangement of FIG. 32, there is provided a second or lower drum assembly 119 mounted in operative arrangement with the upper drum assembly 111 to receive the capsules from the latter and to provide a view of the capsule end opposite to that provided by the upper drum. As shown, lower drum 119 has associated therewith a second or lower optical sensor head array 120, arranged to view the capsules passing therebeneath "end-on", and also a guide plate 121 having similar function to plate 117. In each case, the end-on view is brought about by the slots in the drum which receive the capsules from the hopper. It is intended here that the drums 111, 119 would have slots which are able to readily receive the capsules and yet present the capsules such that the axes of symmetry thereof are substantially perpendicular to the cylindrical surface of the drums, thus providing fully the end-on view.

The two-drum (111, 119) arrangement is positioned as shown relative to the horizontal portion of the total transport system.

In operation, each capsule is placed into a slot of the first drum and its exposed end viewed by an optical sensor head. Then the capsule will move around the drum in the direction indicated and under the guide plate to be transferred to the second drum, where its other end will be exposed and viewed by a second sensor head. Finally, the capsule will be moved around the second rotating drum in the direction indicated under the lower guide plate, to be transferred from the second drum to the horizontal transport. Comparison with standards of the signatures obtained from all sensors which view the capsule can now be made to determine if the capsule is acceptable. It will be apparent that any changes needed or desired in the defect detection routine to fully utilize this end-on viewing aspect of the invention are well within the normal skills of the artisan in this field, having as a guide the within disclosure.

Other embodiments and arrangements of this invention will become apparent to those of skill in this art from this disclosure. For example, rather then having the capsules transported in a direction parallel to their symmetrical axes, the capsules could be fed oriented at an angle with respect to their symmetrical axes, particularly perpendicular thereto. Specifically, with regard to perpendicular capsule orientation relative to the feed flow, this could involve, for example, the simultaneous color and defect inspections of both halves of the capsule. Of course, the reference or standard signatures of a capsule when approached "from the side" will be different from the signatures characteristic of inspection from the "parallel" orientation considered hereinabove. It is, based on the teachings herein, now but a mere task to develop characteristic signatures of good capsules and recognizing the outstanding features thereof for the color and defect inspections. Armed with these standards and being aware of the significant and outstanding features thereof, the system can readily be programmed accordingly to effect highly reliable color recognition and defect detection.

Another alternative would be to provide defect detection optical sensors arranged so as to view the ends of the capsules as they pass by with their axes of symmetry substantially perpendicular to the direction of movement as they move along the horizontal (flat movement) portion of the transport. It is to be understood that the above and other like arrangements are well within the scope of this invention.

What is claimed is:

1. Apparatus for the automated surface analysis of single- and multi-colored objects such as pharmaceutical dose forms based on a standard representative of desired color(s) and a time varying shape signature standard, and for classifying the objects as acceptable or non-acceptable comprising:
   (a) first means including electro-optic means for receiving electromagnetic radiation from an object and for converting same into corresponding electrical signals including signals constituting at least one color vector of the object and signals constituting the time-varying shape signature of the object, and further including means for effecting relative translational movement between said electro-optic means and the objects and for providing output signals which are utilized in determining the instantaneous relative location of the object;
   (b) second means for storing a standard signal representative of the desired object color and a standard time-varying signal representative of the desired object shape; and
   (c) third means operatively connected to said first and second means for comparing the derived signals of the object with the stored standard signals and determining therefrom the acceptability/non-acceptability of that object.

2. Apparatus according to claim 1 wherein said first means is further comprised of electro-optic means including light source means for illuminating the objects and photodetecting means arranged to receive light reflected from the objects in one or more bands of the light spectrum,
   said second means being comprised of means for storing a pre-established standard for each said one or more bands of the spectrum representative of the correct object color(s) and a pre-established standard representative of the correct shape of the object, and
   said third means being comprised of fourth means operatively connected to said electro-optic means and said means for effecting relative movement for selectively sampling the signal generated by said electro-optic means based at least in part on object location and processing said sampled signals into a form representative of object color(s) and shape.

3. Apparatus according to claim 1 wherein said first means includes means for receiving diffusely reflected light from the object in a plurality of different color bands of the electromagnetic radiation spectrum and for providing for each an output signal representative thereof, and means for receiving specularly reflected light from the object and for providing an output signal representative thereof, and fourth means for sampling signals from said means for receiving diffusely reflected light and said means for receiving specularly reflected light and for processing same respectively into a form representative of the desired color(s) and shape signature of the object.

4. Apparatus according to claim 3 further including means connected between said electro-optic means and said third means for converting said electrical signals from said electro-optic means to a first processable form for selective input to said third means and wherein said third means includes controller means for selecting which signals from said electro-optic means are to be converted based at least in part on object location.

5. Apparatus according to claim 4 wherein said third means further includes means for determining the presence of at least a certain characteristic in the electrical signals output from said electro-optic means which serves as a basis for controlling the conversion of the electro-optic output signals.

6. Apparatus according to claim 3 wherein said third means further includes means for storing the processed signals from said means associated to said diffusely reflected light for each of L number of acceptable objects inspected and means for up-dating the stored color(s) standard based on the processed signals of said L acceptable objects.

7. Apparatus according to claim 3 further including means operatively connected to said second means and said third means for separating non-acceptable objects from acceptable objects.

8. Apparatus according to claim 3 wherein said means for effecting relative translational movement constitutes high-speed, continuous-movement transport means for providing automatic on-the-fly inspection of the objects.

9. Apparatus according to claim 8 wherein said transport means includes means for providing the transport of the objects past said electro-optic means in a plurality of flow channels.

10. Apparatus according to claim 9 including a separate electro-optic means for each said flow channel.

11. Apparatus according to claim 10 wherein said means for receiving diffusely reflected light comprises a separate photodetecting means for each of said bands of the electromagnetic radiation spectrum, and said means for receiving specularly reflected light comprises a pair of photodetecting means arranged, in relation to the direction of relative object movement, to receive specularly reflected light from respective different portions of an object.

12. Apparatus according to claim 11 wherein each said photodetecting means operating on said diffusely reflected light has associated therewith a plurality of individual optical channels each intended to inspect a different portion of the object, and each said photodetecting means operating on said specularly reflected light has associated therewith an individual optical channel, one arranged to inspect the front portion of the object and the other the rear portion of the object relative to the direction of object movement.

13. Apparatus according to claim 12 wherein the plurality of optical channels associated with each photodetecting means operating on said diffusely reflected light are arranged to provide inspection of contiguous areas of the object.

14. Apparatus according to claim 3 wherein the objects are capsule dose forms having one portion thereof of one color and at least one other portion thereof of a different color and said means for effecting relative translational movement inclues means for presenting the capsule dose forms to said electro-optic means in a plurality of flow channels with a preferential orientation with respect to their major axes of symmetry, and wherein said electro-optic means comprises at least one optical head arrangement for each flow channel positioned to inspect the capsule dose forms associated with said flow channel, said optical head arrangement including a plurality of optical channels for viewing the objects at different angles.

15. Apparatus according to claim 14 wherein optical channels utilized for color determination are arranged in P groups of R optical channels each and said electro-optic means further comprises a plurality of means for converting optical images obtained by said optical channels to electrical signals, each of a subset of P such converting means including a color filter operative in regard to a predetermined portion of the light spectrum and in operative arrangement with one of said groups of optical channels and photodetecting means arranged to receive the output of said filter and to generate output electrical signals corresponding thereto.

16. Apparatus according to claim 15 wherein said optical channels have associated therewith masking means for providing an optical image of a capsule dose form intended to accentuate at least one certain structural characteristic thereof.

17. Apparatus according to claim 16 wherein said masking means utilizes an elliptical slit possessing major and minor axes to match the contour of a cylindrical portion of the capsule and said optical channels further include lens means having a predetermined aperture and focal length to pass a magnified image of the capsule.

18. Apparatus according to claim 14 wherein a separate photodetecting means is provided for each optical channel utilized for inspection on the basis of shape and wherein each optical channel associated with a separate photodetecting means is predeterminably optically directed relative to the orientation of the capsule dose form for deriving the specular reflectance from respective portions thereof.

19. Apparatus according to claim 18 wherein said optical channels have associated therewith masking means for providing an optical image of a capsule dose form intended to accentuate at least one certain structural characteristic of the capsule dose form.

20. Apparatus according to claim 19 wherein said masking means utilizes a linear slit for accentuating the specular reflectance from the objects, and said optical channels further include lens means having a predetermined aperture and focal length to pass a magnified image of the capsule dose form.

21. System for high speed, continuous automated surface analysis of a batch of capsule dose forms in which such material is classified into acceptable and non-acceptable categories based on both color and shape comprising:

(a) means for derandomizing the capsules and for transporting same in a plurality of streams, with the capsules each having a predetermined orientation with respect to their major axes of symmetry and relative to their direction of movement;

(b) a plurality of light source means at least one of which is arranged relative to each capsule stream for providing light to illuminate the capsules of the associated stream;

(c) a plurality of optical head means at least one of which is associated with each capsule stream for directing light from said source onto the objects of the associated stream, each said optical head means having associated therewith a plurality of optical channel means transmitting in respect to each capsule light reflected from segments of the illuminated portion thereof;

(d) a plurality of optical filter means for filtering the light received from predetermined ones of said optical channel means, each said optical filter means being selected to pass light energy within a respective preestablished frequency range;

(e) first converting means for converting the optical signals of said filter means to respective electrical signals;

(f) means for analyzing said electrical signals relative to references representative of the desired color and shape of the capsules and for generating output signals in response thereto;

(g) said first converting means and said analyzing means comprising color vector forming means wherein the color of an illuminated portion of a capsule is quantified by said color vector forming means; and (h) means for separating the acceptable and non-acceptable capsules in dependence upon said output signals.

22. System according to claim 21 wherein said streams are parallel.

23. System according to claim 21 further including second converting means for converting electrical signals from the first converting means to digital signals.

24. System according to claim 21 wherein said analyzing means is a properly programmed computer.

25. System according to claim 21 wherein said separating means includes multiple air jets for diverting the non-acceptable capsules from the plurality of capsule streams into a plurality of parallel reject channels and shield means for assuring diversion of a capsule from one stream will not interface with capsules in another stream.

26. System according to claim 21 wherein said transporting means provides continuous linear movement of the capsules relative to the optical head means.

27. System according to claim 26 wherein said transporting means moves the capsules aligned with their major axes of symmetry in the direction of motion.

28. System according to claim 21 wherein each said optical channel means is comprised of a mask which is opaque except for at least one slit of predetermined shape and a lens of predetermined aperture and focal length for passing a magnified image of the capsule'a contour.

29. System according to claim 28 wherein said slit is an elliptical slit possessing the proper major and minor axes to match the contour of a cylindrical portion of a capsule.

30. System according to claim 28 wherein said slit is of such geometry as to accentuate the changes of slope along the ends of a capasule.

31. System according to claim 21 wherein said color vector means includes means for forming a set of electrical signals where each signal of the set is proportional to a component of a color vector.

32. System according to claim 31 wherein said first converting means includes a plurality of photodetecting means and wherein the arrangement of said plurality of optical channel means and said photodetecting means is such that the color vector components are generated by passing light from the optical channel means through the set of optical filters having pass bands in different regions of the optical spectrum and detecting the light level of the light passing through each optical filter individually with respective photodetectors, the current output of each photodetector being representative of a component of the color vector.

33. System according to claim 31 wherein the arrangement of said optical channels and said filter means is such that spatial averaging of the illuminated portion of a capsule is provided by passing light reflected from different segments of the illuminated portion of the capsule through common optical filters, to thereby minimize the effects of printing which may be present on at least one such segment.

34. Apparatus for the automated surface analysis of single and multicolored objects such as pharmaceutical dose forms, including the determination of the correctness of the color(s) and shape of the objects relative to respective standards, and classifying the objects into acceptable and nonacceptable categories, comprising:
(a) electro-optic means for receiving electromagnetic radiation from an object and for generating in response thereto electrical signals representative of color and shape, including means for illuminating the object and first means for receiving electromagnetic radiation from the object in at least one band of the electromagnetic radiation specturm and for providing for each a time-varying output signal representative thereof;
(b) second means for effecting relative translational movement between said electro-optic means and the objects and for providing output signals which are utilized in determining the instantaneous relative location of the objects; and
(c) third means connected to said electro-optic means and said second means for selectively sampling the signals from said first means at least in part in dependence on object location and for processing said sampled signals from said first means into a form representative of the color(s) and shape of the object, said third means including fourth means for storing a first standard representative of the desired color(s) of the object and a second, time-varying standard representative of the desired shape of the object, and fifth means for comparing the processed sample signals representative of the color(s) and constituting the time-varying shape signature of the object respectively with said first and second standards and for generating an output signal representative of the acceptability or nonacceptability of each object.

35. System for high-speed, continuous automated surface analysis of a batch of capsule dose forms in which such material is classified into acceptable and non-acceptable categories based on both color and shape comprising:
(a) means for derandomizing the capsules and for transporting same in a plurality of streams, with the capsules each having a predetermined orientation with respect to their major axes of symmetry and relative to their direction of movement;
(b) a plurality of light source means at least one of which is arranged relative to each capsule stream for providing light to illuminate the capsules of the associated stream;
(c) a plurality of optical head means at least one of which is associated with each capsule stream for directing light from said source onto the objects of the associated stream, each said optical head means having associated therewith a plurality of optical channel means transmitting in respect to each capsule light reflected from segments of the illuminated portion thereof;
(d) a plurality of optical filter means for filtering the light received from predetermined ones of said optical channel means, each said optical filter means being selected to pass light energy within a respective pre-established frequency range;
(e) first converting means for converting the optical signals of said filter means to respective electrical signals;
(f) means for analyzing said electrical signals relative to references representative of a desired color and shape of the capsules and for generating output signals in response thereto, said analyzing means including means for determining color vectors of the first and second halves of the capsules by sampling the color vectors generated from different portions along the longitudinal axes of each capsule half and averaging said samples values; and
(g) means for separating the acceptable and nonacceptable capsules in dependence upon said output signals.

36. System for high-speed continuous automated surface analysis of a batch of capsule dose forms in which such material is classified into acceptable and nonacceptable categories based on both color and shape comprising:
(a) means for derandomizing the capsules and for transporting same in a plurality of streams, with the capsules each having a predetermined orientation with respect to their major axes of symmetry and relative to their direction of movement;
(b) a plurality of light source means at least one of which is arranged relative to each capsule stream for providing light to illuminate the capsules of the associated stream;
(c) a plurality of optical head means at least one of which is associated with each capsule stream for directing light from said source onto the objects of the associated stream, each said optical head means having associated therewith a plurality of optical channel means transmitting in respect to each capsule light reflected from segments of the illuminated portion thereof;
(d) a plurality of optical filter means for filtering the light received from predetermined ones of said optical channel means, each said optical filter means being selected to pass light energy within a respective pre-established frequency range;

(e) first converting means for converting the optical signals of said filter means to respective electrical signals;

(f) means for analyzing said electrical signals relative to references representative of a desired color and shape of the capsules and for generating output signals in response thereto, said analyzing means including means for determining whether a capsule is an acceptable color by comparing the generated capsule half color vectors to previously determined acceptable ranges of said vectors, said determining means having means for considering two sets of acceptable ranges, one for cap-first-oriented capsules and one for body-first-oriented capsules; and (g) means for separating the acceptable and nonacceptable capsules in dependence upon said output signals.

37. System for high speed, continuous automated surface analysis of a batch of capsule dose forms in which such material is classified into acceptable and non-acceptable categories based on both color and shape comprising:

(a) means for derandomizing the capsules and for transporting same in a plurality of streams, with the capsules each having a predetermined orientation with respect to their major axes of symmetry and relative to their direction of movement;

(b) a plurality of light source means at least one of which is arranged relative to each capsule stream for providing light to illuminate the capsules of the associated stream;

(c) a plurality of optical head means at least one of which is associated with each capsule stream for directing light from said source onto the objects of the associated stream, each said optical head means having associated therewith a plurality of optical channel means transmitting in respect to each capsule light reflected from segments of the illuminated portion thereof;

(d) a plurality of optical filter means for filtering the light received from predetermined ones of said optical channel means, each said optical filter means being selected to pass light energy within a respective pre-established frequency range;

(e) first converting means for converting the optical signals of said filter means to respective electrical signals;

(f) means for analyzing said electrical signals relative to references representative of desired color and shape of the capsules and for generating output signals in response thereto;

(g) means for separating the acceptable and non-acceptable capsules in dependence upon said output signals;

(h) said analyzing means including means for constructing signatures representative of a capsule's shape by sampling at certain times transformed outputs of certain ones of said optical channel means, said analyzing means being arranged to quantify the shape of a viewed capsule by computing certain predefined parameters of signatures and to determine if a viewed capsule is acceptable by way of means for comparing computed signature parameters to previously determined acceptable ranges.

38. Method for automatically determining the colors of objects of pre-established shape and having at least two distinct major portions thereof of different color, said determination being substantially independently of the sequence in which the different colored portions of the objects are encountered, comprising:

(a) providing a light source to illuminate the objects;

(b) conveying the objects past the light source so as to enable the differently colored portions thereof to be illuminated;

(c) optically scanning each object based at least in part on the relative instantaneous location thereof to provide a plurality of output signals representative of the diffuse reflectance received by said optical scanning in a corresponding number of different portions of the light spectrum for each colored portion of the object;

(d) prestoring reference signals representative of each object color which may be encountered; and (e) comparing the signals derived through optically scanning the object with said reference signals to provide an output indicative of the colors of the object.

39. Method according to claim 38 wherein the objects undergoing color recognition are multicolored objects of known shape having printing thereon of yet another color.

40. Method according to claim 39 characterized by the steps of:

providing a plurality of optical channels for viewing the illuminated objects, arranged in P groups of R channels each;

arranging the R channels of each group relative to the object to receive diffusely reflected light from substantially contiguous portions of the object at substantially the same time;

transmitting for each of said P groups the diffusely reflected light received by each of the R channels thereof to respective ones of P light filters each operatively associated with a different portion of the light spectrum;

providing P photodetector means each associated with one of said filters and deriving therefrom for each group a composite electrical signal representative of a spatially averaged color of each colored portion of the object; and comparing the composite electrical signals to previously determined acceptable ranges.

41. An arrangement for comparing the colors of solid discrete particular objects which are multicolored in predetermined manner to standards representative of a desired multicolor combination and for classifying on the basis of color comparison the objects as acceptable or non-acceptable comprising:

(a) light source means for illuminating the objects and first means for detecting diffusely reflected light from an object in each of N distinct spectral bands for each colored portion of the objects, where $N \geq 3$, and converting same to N respective electrical signals for each said colored portion to thereby form a color vector in electrical signal form for each colored portion of the object;

(b) second means for storing a plurality of standard color vectors representative of the desired multicolor combination for the objects; and (c) third means connected to said first and second means for comparing the derived color vectors of an object with the standard color vectors and determining therefrom whether that object is acceptable or non-acceptable.

42. An arrangement according to claim 41 further including means for storing the derived color vector signals for the previous M number of acceptable objects and for up-dating the stored standard color vectors based on these stored derived color vectors.

43. An arrangement according to claim 41 wherein the objects are capsule dose forms having one portion thereof of one color and the other portion thereof of another color, and wherein said third means includes means for determining whether the one color vector associated with the one color portion of a capsule dose form corresponds to one of the standard color vectors and whether the color vector associated with the other portion of the capsule dose form corresponds to the other of the standard color vectors.

44. An arrangement according to claim 41 further including means for separating the non-acceptable objects from the acceptable objects.

45. An arrangement according to claim 41 further including means for providing an incrementally up-dated count of the acceptable objects.

46. Apparatus for the automated surface analysis, in particular the color(s), of single and multicolored objects such as pharmaceutical dose forms based on a standard representative of desired color(s), and for classifying the objects as acceptable or non-acceptable, comprising:
(a) first means comprising light source means for illuminating the objects and means for receiving electromagnetic radiation from preselected portions of the surface of an object based on the shape of the object and for converting same into electrical signals, said receiving means including photodetecting means arranged to receive light reflected from the objects in a plurality of color bands of the light spectrum, said first means further comprising means for effecting relative movement between said electro-optic means and the object and for providing output signals which are utilized in determining the instantaneous relative location of the object;
(b) second means for storing a standard signal representative of the desired object color(s), said second means being comprised of means for storing a pre-established standard for each of said bands of the spectrum representative of the desired object color(s); and
(c) third means operatively connected to said first and second means for comparing derived signals of the object with the stored standard signal and determining therefrom and acceptability/non-acceptability of that object, said third means being comprised of fourth means, operatively connected to said electro-optic means and said means for effecting relative movement, for selectively sampling the signals generated by said electro-optic means based at least in part on object location and processing said sampled signals into a form representative of object color(s).

47. Apparatus according to claim 46 wherein the objects are multicolored in predetermined manner and the standards are representative of a desired multicolor combination, and wherein said electro-optic means includes means for detecting diffusely reflected light from an object in each of N distinct spectral bands for each colored portion of the objects where $N \geq 3$, and converting same to N repsective electrical signals for each said color portion to thereby form a color vector in electrical signal form for each colored portion of the object, and said second means includes means for storing a plurality of standard color vectors representative of the desired multicolor combination of the objects for comparison to the derived color vectors of an object.

48. Apparatus according to claim 47 wherein said third means includes means for determining the relative order of appearance of the colors of an object and comparing same to the stored standards.

49. Apparatus according to claim 46 wherein said means for effecting relative movement is comprised of high-speed, continuous-movement transport means for providing on-the-fly inspection of the objects.

50. Apparatus according to claim 49 wherein said transport means includes means for providing transport of the objects past said electro-optic means in a plurality of flow channels.

51. Apparatus according to claim 50 wherein said electro-optic means includes a separate photodetecting means and light source means for each flow channel provided by the transport means.

52. Apparatus according to claim 51 wherein said photodetecting means includes a separate photodetector for each of said spectrum bands.

53. Apparatus according to claim 52 wherein said separate photodetector has associated therewith a plurality of individual optical channels each arranged to inspect a different portion of the object to provide a spatial averaging of the output of said photodetector.

54. Apparatus according to claim 53 wherein the plurality of optical channels are arranged to provide inspection of contiguous areas of the object.

55. Apparatus according to claim 46 futher including means coupled between said electro-optic means and said means for effecting relative movement, for converting said electrical signals from said electro-optic means to a first processable form for selective input to said means for effecting relative movement.

56. Apparatus according to claim 55 wherein said third means further includes means for determining the presence of at least a certain characteristic in the electrical signals output from said electro-optic means which characteristic serves as a basis for controlling the conversion of the electro-optic signals.

57. Apparatus according to claim 56 wherein said third means further includes means for storing in convenient retrievable form the signal values obtained for N previously analyzed acceptable objects and means for up-dating the stored standards based on the values obtained for said N acceptable objects.

58. Apparatus according to claim 46 wherein said third means further includes counter means for providing an incrementally up-dated count of the analyzed objects deemed acceptable and for providing a total count of acceptable objects inspected at the end of the inspection run.

59. Apparatus according to claim 46 further including means operatively connected to said means for effecting relative movement and to said third means for separating non-acceptable objects from acceptable objects.

60. Apparatus according to claim 46 wherein the objects are capsule dose forms having one portion thereof of one color and at least one other portion thereof of the same or different color and said means for effecting relative movement includes means for presenting the capsule dose forms to said electro-optic means in a plurality of flow channels with each capsule dose form in a preferential orientation with respect to its major axis of symmetry, and wherein said electro-optic means comprises at least one optical head arrangement for each flow channel positioned to inspect the capsule forms associated with said flow channel, said optical head arrangement including a plurality of optical channels for viewing the articles at different angles.

61. Apparatus according to claim 60 wherein said electro-optic means further comprises a plurality of means for converting optical images obtained by said optical channels to electrical signals, each said optical image converting means including a color filter operative in regard to a predetermined portion of the light spectrum and arranged to receive the images of at least some of the optical channels and said photodetecting means arranged to receive the images from said filter for generating electrical output signals corresponding to the light images input thereto, and wherein said optical channels are arranged in P groups of R optical channels each, with a respective optical image converting means being associated with each of said P groups.

62. Apparatus according to claim 61 wherein said optical channels have associated therewith masking means for providing an optical image of a capsule dose form intended to accentuate at least one certain structural characteristic of the capsule dose form.

63. Apparatus according to claim 61 wherein for each optical image converting means the output signals therefrom derived from a capsule dose form and time-referenced over an inspection period thereof constitute the color signature portion of that capsule dose form for the associated group of optical channels, and wherein said third means includes means for comparing the composite signature obtained from the output signals of said plurality of image converting means to a reference signature stored therein and thereby determining the acceptability/non-acceptability of that capsule dose form.

64. An arrangement for determining the correctness of color(s) of articles relative to a standard and classifying said articles into acceptable and non-acceptable categories, comprising:
(a) electro-optic means including light source means for illuminating the articles and photodetecting means arranged to receive light reflected from the articles in at least three color bands of the light spectrum and for generating electrical signals corresponding thereto;
(b) first means for effecting relative movement between said electro-optic means and the articles and for providing output signals which are utilized in determining the instantaneous relative location of the articles; and
(c) control sampling and processing means operatively connected to said electro-optic means and said first means for selectively sampling the signals generated by said electro-optic means and derived from a predetermined plurality of different surface areas of an article based at least in part on article location and processing said sampled signals into a form representative of article color(s), said control sampling and processing means including means for storing a pre-established reference for each of said bands of the spectrum representative of the correct article color(s), and means for comparing the processed sampled signals associated to the respective spectrum bands to corresponding ones of said references and for generating output signals representative of the acceptability/non-acceptability of each article.

65. Apparatus for the automated surface analysis of multicolored objects, such as pharmaceutical dose forms, including the determination of the correctness of the color of each observed colored portion of the objects relative to a standard, and classifying the objects into acceptable and non-acceptable categories, comprising:
(a) electro-optic means for receiving electromagnetic radiation from each colored portion and for generating in response thereto electrical signals representative of color, including means for illuminating the object and first means for receiving electromagnetic radiation from the object in a plurality of different color bands of the electromagnetic radiation spectrum and for providing for each an output signal representative thereof;
(b) second means for effecting relative movement between said electro-optic means and the objects and for providing output signals which are utilized in determining the instantaneous relative location of the objects; and
(c) third means connected to said electro-optic means and said second means for selectively sampling the signals from said first means at least in part in dependence on object location and for processing said sampled signals from said first means into a form representative of the colors of the object, said third means including fourth means for storing standards representative of the desired colors of the object and fifth means for comparing the processed sampled signals representative of the colors of the object with said standards and for generating an output signal representative of the acceptability or non-acceptability of each object irrespective of the order in which the colored portions of the objects are presented to said electro-optic means.

66. A method of automated surface inspection of objects of known shape for surface defects, comprising:
(a) providing a light source for illuminating the objects;
(b) translationally conveying the objects relative to the light source for illuminating same, said object being conveyed in predetermined orientation relative to the major axis of symmetry thereof;
(c) providing an electro-optical system relative to the direction of movement of the objects arranged to receive specular reflectance from an object as the same is illuminated by said light source and obtaining thereby a time-varying electrical signal representative of the object shape; and
(d) analyzing said electrical signals based on a standard representative of desired object shape.

67. Apparatus for the automated surface analysis of objects, such as pharmaceutical dose forms, including the determination of the correctness of the shape of the objects relative to a time-varying standard shape signature, and classifying the objects into acceptable/non-acceptable categories, comprising:
(a) electro-optic means for receiving electromagnetic radiation from an object and for generating in response thereto electrical signals representative of shape, including means for illuminating the object and first means for receiving electro-magnetic radiation from the object in at least one band of electromagnetic radiation spectrum and for providing for each an output signal representative thereof;
(b) second means for effecting relative translational movement between said electro-optic means and the objects and for providing output signals which are utilized in determining the instantaneous relative location of the objects; and (c) third means connecting to said electro-optic means and said second means for selectively sampling the signals from said first means at least in part in dependence an object location and for processing said sampled signals from said first means into a form representative of the shape of the object, said third means including fourth means for storing a time-varying standard shape signature representative of the desired shape of the object, and fifth means for comparing the processed sampled signals constituting the time-varying shape signature of the object with said standard and for generating an output signal representative of the acceptability or non-acceptability of each object.

68. Apparatus according to claim 67 wherein said electro-optic means includes means for accentuating the specular reflectance from the article.

69. Apparatus according to claim 68 wherein said third means further includes counter means for providing an incrementally up-dated count of the inspected objects deemed acceptable and for providing a total count of acceptable objects inspected at the end of an inspection run.

70. Apparatus according to claim 68 further including means operatively connected to said second means and to said third means for separating non-acceptable objects from acceptable objects.

71. Apparatus according to claim 68 further including means coupled between said electro-optic means and said third means for converting the output signals from said electro-optic means to a first processable form for selective input to said third means, and wherein said third means includes controller means for selecting which signals from said electro-optic means are to be converted based at least in part on object location.

72. Apparatus according to claim 71 wherein said third means further includes means for determining the presence of at least a certain characteristic of the electrical signals output from said electro-optic means which characteristic serves as a basis for controlling the conversion of the electro-optic output signals.

73. Apparatus according to claim 68 wherein said second means constitutes high-speed continuous-movement transport means for providing on-the-fly inspection of the objects.

74. Apparatus according to claim 73 wherein said transport means includes means for providing the transport of the objects past said electro-optic means in a plurality of flow channels.

75. Apparatus according to claim 74 wherein said electro-optic means includes a separate photodetecting means and light source means for each flow channel of the transport means.

76. Apparatus according to claim 75 wherein said photodetecting means includes a pair of optical channels arranged relative to the direction of objects movement for sensing the specular reflectance respectively from the frontal and rear portions of the objects.

77. Apparatus according to claim 76 wherein each said optical channel has associated therewith a separate photodetector.

78. Apparatus according to claim 68 wherein the objects are capsule dose forms having a cap portion and a body portion and said second means includes means for presenting the capsule dose forms to said electro-optic means in a plurality of flow channels with each capsule dose form in a preferential orientation with respect to its major axis of symmetry, and wherein said electro-optic means comprises at least one optical head arrangement for each flow channel positioned to inspect the capsule dose forms associated with said flow channel, said optical head arrangement including a plurality of optical channels predeterminably optically directed relative to the orientation of the capsule dose forms for deriving the specular reflectance from respective different portions of the capsule dose forms.

79. Apparatus according to claim 78 wherein said optical channels have associated therewith masking means for providing an optical image of a capsule dose form intended to accentuate at least one certain structural characteristic thereof.

80. Apparatus according to claim 78 wherein said electro-optic means further comprises a plurality of means in one-to-one correspondence with the optical channels for converting the radiation received by said optical channels into electrical signals representative thereof.

81. Apparatus according to claim 80, wherein said electro-optic means is operative at least partially in the infrared light spectrum.

82. Apparatus according to claim 80 wherein the electrical signals from said plurality of converting means derived from a capsule dose form and time-referenced over an inspection period thereof constitute the shape signature of that capsule dose form, and wherein said third means includes means for comparing said shape signature to a standard signature stored therein representative of the correct capsule dose form shape.

83. Apparatus for comparing the shape of solid discrete particular objects to standard representative of a desired shape and for classifying the objects as acceptable or non-acceptable on the basis of said comparison, comprising:

(a) first means for sensing the specular reflectance from a plurality of predetermined portions of an object, said portions being selected on the basis of the desired object's shape, and for converting same into respective electrical signals, said plurality of electrical signals collectively constituting a time-varying shape signature of that object;

(b) second means for storing a time-varying standard shape signature of the desired object shape; and (c) third means connected to said first and second means for comparing the derived signature of the object with the stored standard signature and determining therefrom the acceptability/non-acceptability of that object.

84. Apparatus according to claim 83 wherein the objects are assembled capsule dose forms and said first means includes first and second sensing means for sensing the specular reflectance respectively from the front and rear portions of the capsule dose forms relative to the direction of movement of the same and the major axes of symmetry thereof.

85. Apparatus according to claim 83 further including means for separating the non-acceptable from the acceptable objects.

86. Apparatus according to claim 23 further including means for providing an incrementally up-dated count of the acceptable capsule dose forms.

87. Apparatus for determining the correctness of shape of articles relative to a time-varying shape signature standard and classifying said articles into acceptable and non-acceptable categories, comprising:
(a) electro-optic means including light source means for illuminating the articles and photodetecting means arranged to receive light reflected from the articles and for generating electrical signals corresponding thereto, said photodetecting means having means for accentuating the specular reflectance from the articles;
(b) first means for effecting relative translational movement between said electro-optic means and the articles and for providing output signals which are utilized in determining the instantaneous relative location of the articles; and
(c) control sampling and processing means connected to said electro-optic means and said first means for selectively sampling the signals generated by said electro-optic means based at least on part on article location and processing said sampled signals into a form representative of article shape, said control sampling and processing means including means for storing a pre-established time varying reference signal representative of the correct shape of the articles and means for comparing the processed sample signal constituting the time-varying shape signature of an article with the stored reference and for generating an output signal representative of the acceptability or non-acceptability of each article.

* * * * *